United States Patent [19]

Ieoka

[11] Patent Number: 5,007,408
[45] Date of Patent: Apr. 16, 1991

[54] ENDOSCOPE LIGHT SOURCE APPARATUS

[75] Inventor: Shouichi Ieoka, Hachioji, Japan

[73] Assignee: Olympus Optical Co., Ltd., Tokyo, Japan

[21] Appl. No.: 432,642

[22] Filed: Nov. 7, 1989

[30] Foreign Application Priority Data

Mar. 16, 1989 [JP] Japan .................................. 64-65056
Oct. 12, 1989 [JP] Japan ................................ 64-267183

[51] Int. Cl.⁵ .............................................. A61B 1/06
[52] U.S. Cl. .......................................... 128/6; 358/98
[58] Field of Search ...................... 128/6, 634; 358/98

[56] References Cited

U.S. PATENT DOCUMENTS

| | | | |
|---|---|---|---|
| 4,331,403 | 5/1982 | Ohno | 128/6 |
| 4,625,236 | 11/1986 | Fujimori et al. | 128/6 |
| 4,653,478 | 3/1987 | Nagasaki et al. | 128/6 |
| 4,704,520 | 11/1987 | Kanno et al. | 128/6 |
| 4,821,117 | 4/1989 | Sekiguchi | 128/6 |
| 4,862,258 | 8/1989 | Kidawara et al. | 128/6 |
| 4,866,526 | 9/1989 | Ams et al. | 128/6 |
| 4,870,487 | 9/1989 | Noguchi | 128/6 |
| 4,884,134 | 11/1989 | Tsuji et al. | 128/6 |
| 4,885,635 | 12/1989 | Kimura et al. | 128/6 |
| 4,898,175 | 2/1990 | Noguchi | 128/6 |
| 4,953,539 | 9/1990 | Nakamura et al. | 128/6 |
| 4,959,710 | 9/1990 | Uehara et al. | 358/98 |

FOREIGN PATENT DOCUMENTS 3743920 7/1986 Fed. Rep. of Germany .......... 128/6

*Primary Examiner*—Edward M. Coven
*Assistant Examiner*—Jessica J. Harrison
*Attorney, Agent, or Firm*—Armstrong, Nikaido, Marmelstein, Kubovcik & Murray

[57] ABSTRACT

In the endoscope light source apparatus of this invention, the position within a body cavity of an endoscope tip part can be confirmed with a body outside transmitted light and there are provided an illuminating light feeding apparatus for generating an illuminating light to be fed to the endoscope and a light amount increasing apparatus for increasing for a set time the light amount of the illuminating light generated by the illuminating light feeding apparatus when a body outside light observing signal confirming from outside the body the position within the body cavity of the endoscope tip part is input.

34 Claims, 17 Drawing Sheets

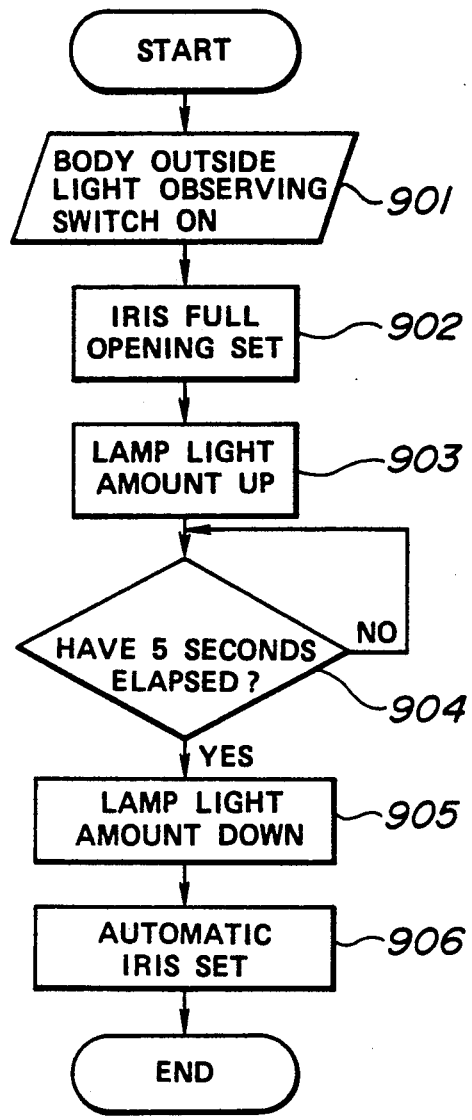
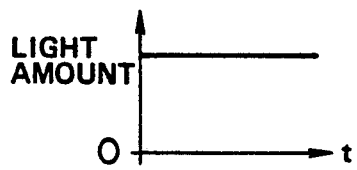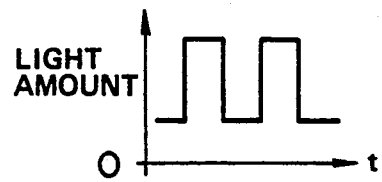

ENDOSCOPE LIGHT SOURCE APPARATUS

FIELD AND BACKGROUND OF THE INVENTION

This invention relates to an endoscope and light source apparatus wherein the position of the tip part of an endoscope insertable part can be confirmed outside the body by means of a transmitted light.

Recently, there is extensively utilized an endoscope (called also a scope or fiber scope) whereby organs within a body cavity can be observed and various therapeutic treatments can be made by using, as required, treating instruments inserted through treating instrument channels.

There are also suggested various electronic scopes using such solid state imaging device as a charge coupled device (CCD).

Among color image imaging systems of such electronic scopes, there are such frame sequential type wherein an illuminating light is sequentially switched to R (red), G (green) and B (blue) as is shown, for example, in the publication of Japanese patent application laid open No. 82731/1986 and such color mosaic type (called also a simultaneous type) wherein a filter array in which color transmitting filters transmitting respectively such color lights as of R, G and B are arranged in the form of a mosaic is provided on the front surface of a solid state imaging device as is shown, for example, in the publication of Japanese patent application laid open No. 76888/1985.

On the other hand, in observing the interior of a body cavity with an endoscope, there is known a technique of confirming the position of the endoscope tip part with an illuminating light emitted from the tip part of the endoscope and transmitted outside the body. However, in confirming the position with such transmitted light, in the above mentioned frame sequential type electronic scope, as the illuminating light is separated into respective color lights by a color separating filter, the illuminating light amount will be reduced to be so low than in the color mosaic type radiating a white color light to the object that it will be hard to confirm the tip position. In order to solve this problem, there is disclosed as shown, for example, in the publication of Japanese patent application laid open No. 2927/1987 a technique of removing the color separating filter from the light path to increase the light amount even when the frame sequential type electronic scope is being used.

However, in case the rotary filter is retreated or merely the light amount is increased as mentioned above, in the electronic endoscope or fiber scope, such a large amount of illuminating light will be radiated to the part to be observed that the observed part has been likely to be burned by the heat of the illuminating light.

OBJECT AND SUMMARY OF THE INVENTION

The present invention has as an object to provide an endoscope light source apparatus whereby the tip part of the endoscope can be confirmed from outside the body without burning the part to be observed.

The endoscope light source apparatus according to the present invention comprises an illuminating light feeding apparatus for generating an illuminating light to be fed to the endoscope and a light amount increasing apparatus for increasing for a set time the light amount of illuminating light generated by the illuminating light feeding apparatus when a body outside light observing signal is input for confirming from outside the body the position within the body cavity of the endoscope tip part.

In the present invention, the illuminating light feeding apparatus feeds an illuminating light to the endoscope. The light amount increasing apparatus increases for a preset time the illuminating light output from the illuminating apparatus with a body outside light observing signal input in confirming the position of the endoscope tip part from outside the body. When the illuminating light fed to the endoscope is increased, the illuminating light radiated into the body cavity from the endoscope tip will be transmitted outside the body so that the position of the endoscope tip part may be confirmed from outside the body. When the light amount of the illuminating light increases, the inside wall of the body cavity will rise in temperature but, before the inside wall of the body cavity burns, the light amount increasing apparatus will decrease the light amount of the illuminating light.

BRIEF DESCRIPTION OF THE DRAWINGS

FIG. 1 is a general explanatory view of an electronic endoscope apparatus.

FIG. 2 is a block diagram showing a general formation of the electronic endoscope in the case of a body outside light observation.

FIG. 3 is a block diagram of the electronic endoscope apparatus in the case of an ordinary observation.

FIG. 4 is an explanatory view of a rotary filter.

FIG. 5 is an explanatory view of a rotary filter moving mechanism.

FIG. 6 is a block diagram of a rotary filter moving circuit.

FIG. 7 is a flow chart for explaining the operation of a light source apparatus.

FIG. 8 is a circuit diagram for transmitting signals between a video processor and light source apparatus.

FIG. 9 is a circuit diagram for controlling an iris with a reference value of an automatic gain control.

FIG. 10 is a circuit diagram for controlling the iris in the case of a device shutter.

FIG. 11 is a block diagram showing the general formation of an electronic endoscope.

FIG. 12 is an explanatory view of a turret filter.

FIG. 13 is a flow chart for explaining the operation of a light source apparatus.

FIG. 16 is an explanatory view of a rotary color filter.

FIG. 17 is a circuit diagram of a motor controlling circuit.

FIG. 21 is a block diagram showing the general formation of an electronic endoscope apparatus.

FIG. 22 is a flow chart for explaining the operation of a CPU.

FIGS. 23 to 25 relate to the tenth embodiment of the present invention.

FIG. 23 is a block diagram of an endoscope apparatus having a fiber scope.

FIG. 24 is a block diagram for explaining the operation of a CPU.

FIG. 25 shows explanatory diagrams of light amounts fed by a light source lamp.

DETAILED DESCRIPTION OF THE PREFERRED EMBODIMENTS OF THE INVENTION

The embodiments of the present invention shall be explained in the following with reference to the drawings.

FIGS. 1 to 10 show the first embodiment of the present invention.

Figure 1:
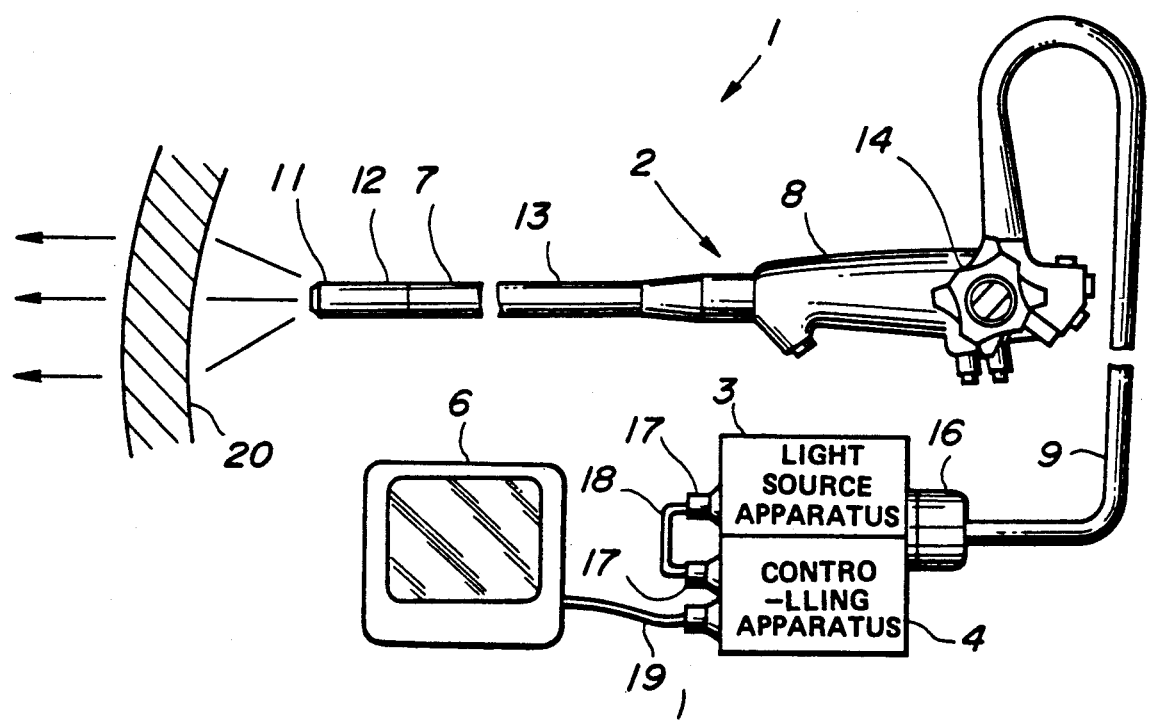
FIGS. 1 to 10 relate to the first embodiment of the present invention.

In FIG. 1, an electronic endoscope apparatus 1 comprises an endoscope 2, a light source apparatus 3 for feeding an illuminating light to this endoscope 2, a controlling apparatus 4 for processing the output signal of the endoscope 2 and a monitor 6 for displaying on a picture surface a video signal output from this controlling apparatus.

The above mentioned endoscope 2 comprises an insertable part 7, a thick operating part 8 connected to this insertable part 7 on the rear end and a light guide and signal cable 9 extended from the side of this operating part 8.

The above mentioned insertable part 7 is provided on the tip with a rigid tip part 11, on the rear side adjacent to this tip part 11 with a curvable part 12 and further in the rear of this curvable part 12 with a flexible part 13. The above mentioned curvable part 12 can be curved vertically and horizontally by operating a curving operation knob 14 provided in the above mentioned operating part 8.

A light guide and signal connector 16 is provided at the rear end of the above mentioned light guide and signal cable 9 so as to be connected simultaneously to the above mentioned light source apparatus 3 and controlling apparatus 4 which are connected with each other through a signal cable 18 provided at both ends with connectors 17. Further, the controlling apparatus 4 is connected to the above mentioned monitor 6 through a signal cable 19.

An illuminating light fed from the above mentioned light source apparatus 3 is emitted forward from the tip part 11 so that a part of this illuminating light may be transmitted through an inside wall 20 of a body cavity.

Figure 2:
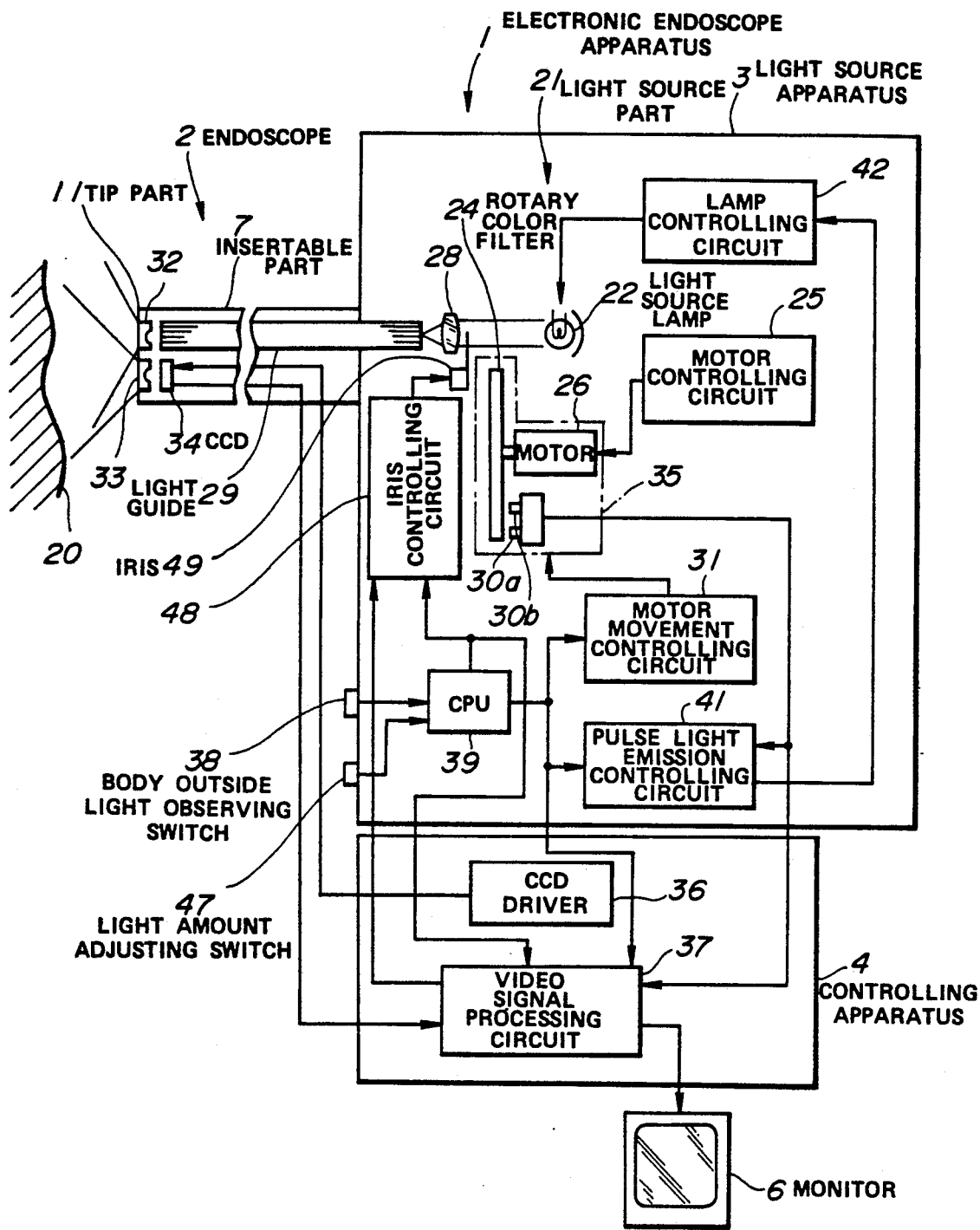
Figure 3:
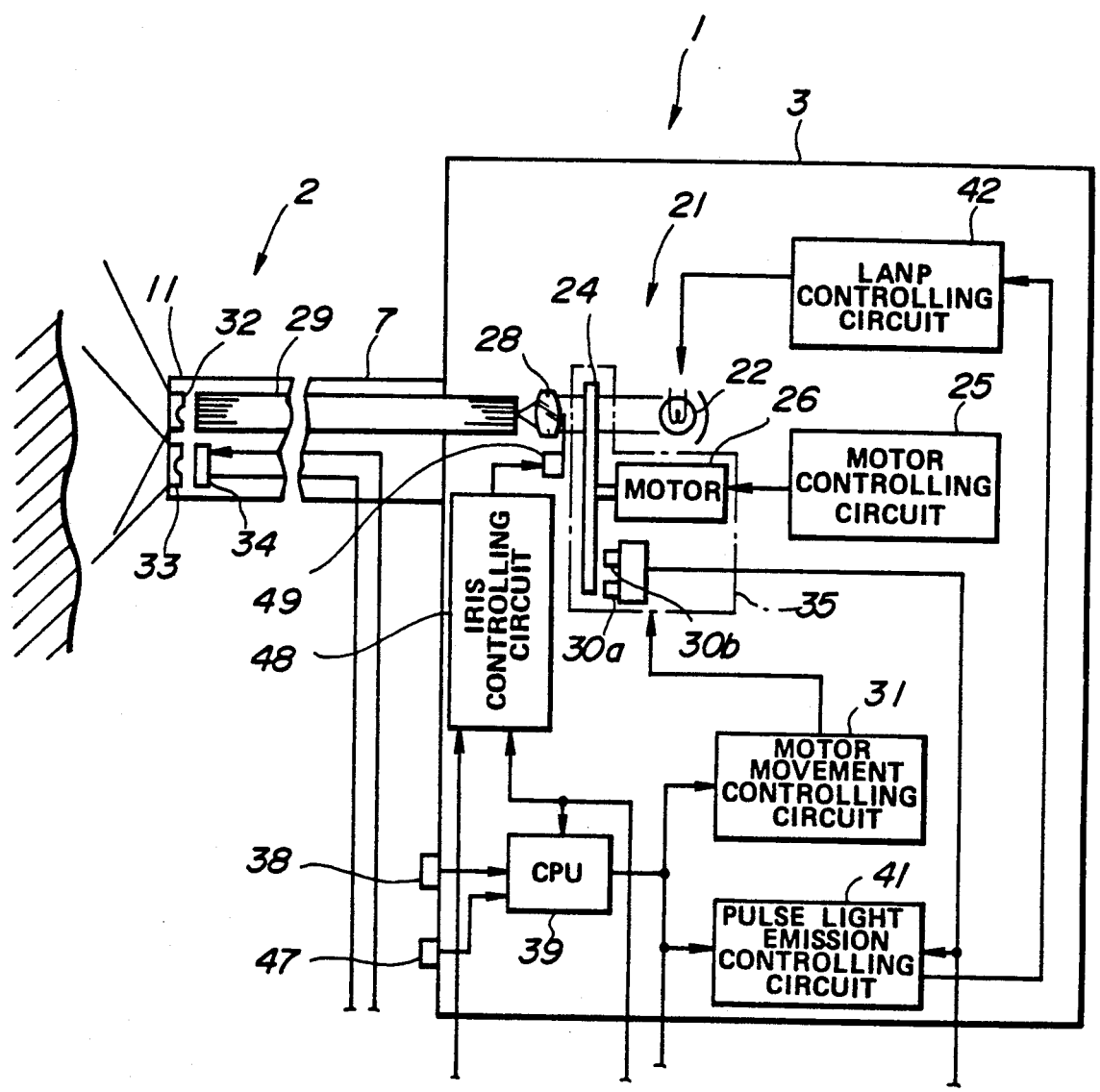

In FIGS. 2 and 3, a light source part 21 is provided with a light source lamp 22 and a rotary color filter 24 having color transmitting filters 23R, 23G and 23B of three primary colors of R (red), G (green) and B (blue). This rotary color filter 24 is rotated and driven by a motor 26 controlled by a motor controlling circuit 25.

The illuminating light emitted by the above mentioned light source lamp 22 is injected into the above mentioned rotary color filter 24. The illuminating light transmitted through this rotary color filter 24 is made color lights of respective wavelengths of red, green and blue, is condensed by a condenser lens 28 and is injected into a light guide 29 on the entrance end surface.

The above mentioned rotary color filter 24 is provided together with the above mentioned motor 26 and photosensors 30a and 30b detecting the positions of the color transmitting filters 23R, 23G and 23B provided in the rotary color filter 24 on a rotary filter block 35 which inserts and removes the rotary color filter 24 into and out of a light path connecting the light source lamp 22 and the entrance end surface of the light guide 29 by the motor movement controlling circuit 31.

Figure 5:
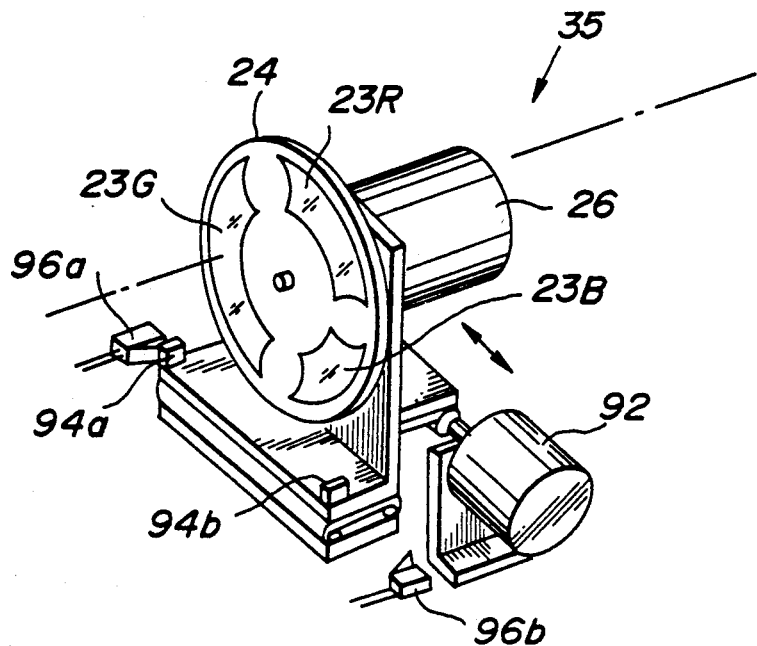
Figure 6:
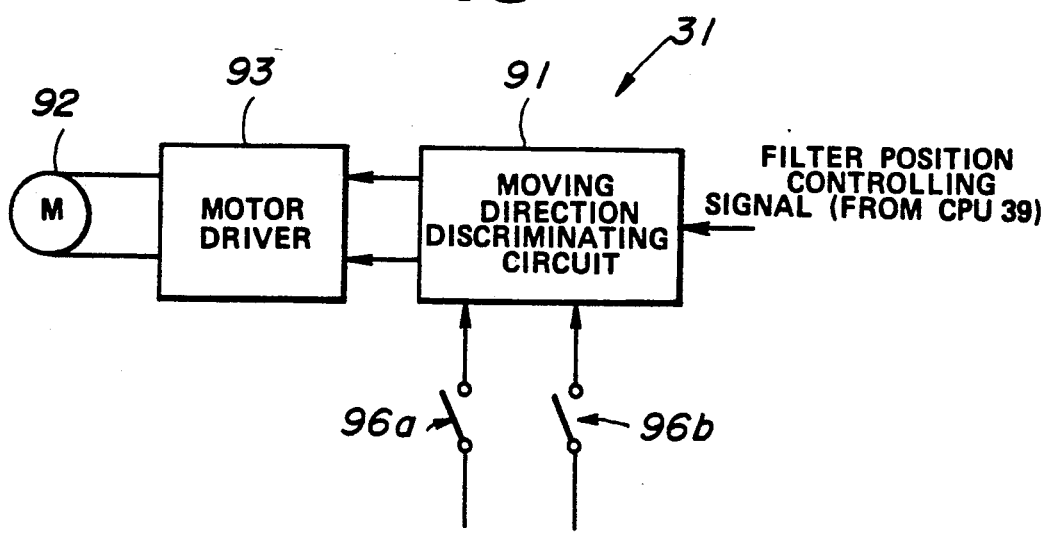

FIG. 5 is a formation view of the above mentioned rotary filter block 35. FIG. 6 is a block diagram of the motor movement controlling circuit 31. In FIGS. 5 and 6, in case the rotary color filter 24 is retreated from the light path, when a filter position controlling signal from a CPU 39 varies to insert the rotary color filter 24 into the light path, a moving direction discriminating circuit 91 of the motor movement controlling circuit 31 will output a signal to a motor driver 93 so that, for example, a moving motor 92 may normally rotate. Thereby, the moving motor 92 will normally rotate and the rotary filter block 35 will be moved so that the rotary color filter 24 may be inserted into the light path. When the rotary color filter 24 is moved into the light path, a switch pressing member 94a will push a limit switch 96a so that the moving direction discriminating circuit 91 may output to the moving motor 92 a signal ordering to stop.

Also, when the filter position controlling signal from the CPU 39 varies to remove the rotary color filter 24 out of the light path, the moving direction discriminating circuit 91 will output a signal to the motor driver 93 so that the moving motor 92 may reversely rotate: When the rotary color filter 24 is removed out of the light path, the switch pressing member 94b will press a limit switch 96b so that the moving direction discriminating circuit may have the moving motor 92 stop the reverse rotation.

The above mentioned motor movement controlling circuit 31 is connected with the CPU 39 for outputting a transillumination signal when an on-signal is input from a body outside light observing switch 38 provided, for example, on the front surface of the light source apparatus 3 so that, when the above mentioned transillumination signal is input, the above mentioned rotary color filter block 35 may be removed out of the light path.

This CPU 39 is connected also to a pulse light emission controlling circuit 41 so as to input the above mentioned transillumination signal. This pulse light emission controlling circuit 41 instructs the lamp controlling circuit 42 receiving the transillumination signal and feeding an electric current to the above mentioned light source lamp 22 to stop the pulse light emission and to continue the light emission.

Further, the CPU inputs the above mentioned transillumination signal also into a video signal processing circuit 37 which receives the transillumination signal, displays in the monitor 6 as a still image an image just before a body outside observation (transillumination) is made, displays in black and white an image read out, for example, at the timing, for example, of G among the three primary color signals R, G and B and displays in the monitor 6 words showing that the transillumination is being made.

A light amount adjusting switch 47 is connected to the CPU 39 which transmits to an iris controlling circuit 48 automatic and manual light amount set values set by the light amount adjusting switch 47. The iris controlling circuit 48 controls an iris 49 with an EE signal from the video signal processing circuit 37 and a light amount set value from the CPU 39. Also, the light amount set value from the CPU 39 is transmitted to the video signal processing circuit 37 and is used as a reference value of an automatic gain controlling circuit (abbreviated as an AGC circuit hereinafter) not illustrated within the video signal processing circuit 37. In the AGC circuit, the reference value of the automatic gain control is varied on the basis of the light amount set value so that, even if the light amount is varied by operating the iris 49, the AGC circuit may make a correction and the brightness on the monitor 6 may be prevented from becoming invariable.

Figure 4:
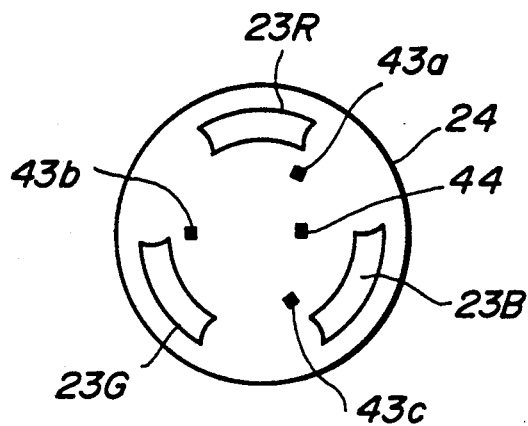

In FIG. 4, marks 43a, 43b and 43c showing the positions of the respective color transmitting filters 23R, 23G and 23B are concentrically circularly provided in the rotating direction of the respective color transmitting filters 23R 23G and 23B of the rotary filter 24. A starting signal mark 44 is provided coaxially with the marks 43a, 43b and 43c to discriminate R, G and B of these marks 43a, 43b and 43c.

On the other hand, the above mentioned light guide 29 is inserted through the endoscope 2 so as to be able to radiate an illuminating light to the inside wall 20 of the body cavity with a light distributing lens 32 arranged in front of the exit end surface of this light guide 29.

The reflected lights corresponding to the respective color lights of red, green and blue from the above mentioned inside wall 20 of the body cavity are transmitted through an objective lens 33 provided in the tip part 11 and are received on the imaging surface of a solid state imaging device (abbreviated as CCD hereinafter) 34 provided in the image forming position of this objective lens 33. An image of an object is photoelectrically converted by this CCD and is sequentially output, for example, horizontally by a driving clock applied from a CCD driver 36 provided within the controlling apparatus 4 An electric signal including this image information is input into the video signal processing circuit 37 within the above mentioned controlling apparatus 4. In this video signal processing circuit 37, the signal is processed to produce a composite video signal which is output to the monitor 6 displaying the observed image.

The operation of the electronic endoscope apparatus 1 formed as mentioned above shall be explained.

The operator inserts the insertable part 7 of the endoscope 2 into a body cavity. The illuminating light emitted from the light source apparatus 3 is sequentially separated into respective color lights of R (red), G (green) and B (blue) and is fed to the light guide 29. The light source lamp 22 pulse-lights as synchronized with the aperture part of the rotary filter 24. The illuminating light fed into the body cavity enters the CCD 34 as a reflected light, the electric charge is accumulated and the electric charge accumulated during the light intercepting period of the rotary color filter 24 is read out by a driving clock applied from the CCD driver 36 and is output to the video signal processing circuit 37 within the controlling apparatus 4. The composite video signal is output to the monitor 6 from this video signal processing circuit 37 and the object image is displayed on the picture surface.

During the inserting operation, in the case of confirming the position of the tip part 11, the operator switches on the body outside light obserting switch 38 provided in the light source apparatus 3. The on-signal is input into the CPU 39 which generates a transillumination signal which is output to the pulse light emission controlling circuit 41 and video signal processing circuit 37.

The motor movement controlling circuit 31 receives the transillumination signal and moves the rotary filter block 35 to retreat the rotary color filter 24 from the light path. By the way, even in case the rotary color filter 24 is in the position retreated from the light path, the motor controlling circuit 25 will rotate and drive the rotary color filter 24.

On the other hand, in case the photosensor 30a detects the marks 43a, 43b and 43c provided in the rotary filter 24 the output signal will be on the L level. Also, when the photosensor 30b detects the starting signal mark 44, the output signal will be on the L level. The output signals of the photosensors 30a and 30b are delivered to the pulse light emission controlling circuit 41 which judges the L level of the photosensor 30b just after the photosensor 30a becomes on the L level to be of the color transmitting filter 23R. The signals of the photosensors 30a and 30b are transmitted to the video signal processing circuit 37 which outputs an image signal to the monitor 6 while this signal is input.

The pulse light emission controlling circuit 41 receives the transillumination signal and outputs to the lamp controlling circuit 42 the stop of the pulse light emission. The lamp controlling circuit 42 stops the feed of the pulse light emitting electric power to the light source lamp 22 which lights with a fixed light amount.

Also, it is not always necessary to stop the pulse light emission. Even during the body outside light observing mode, the pulse light emission may be continued. Further, during the body outside light observing mode, the light amount may be increased.

The video signal processing circuit 37 receives a transillumination signal and outputs to the monitor 6 the image just before making the transillumination as a still image. By the way, other than making a still image, the image read out by the timing of G among the three primary color signals R, G and B may be displayed in black and white and the words showing that the transillumination is being made may be displayed.

Also, the CPU 39 outputs to the iris controlling circuit 48 a signal to set the iris 49 in a proper position. Meanwhile, by operating the light amount adjusting switch 47, the emitted light amount can be varied. Further, the CPU 39 has a timer not illustrated by which the time since the body outside light observing switch 38 is switched on is counted so that, when the time, for example, of 5 seconds at which a burn is considered to be generated by the increase of the illuminating light amount has elapsed, the output of the transillumination signal may be automatically stopped, the rotary filter 24 may be inserted into the light path, the pulse light emission may be resumed and the iris 49 may be set at a value as before the transillumination is made.

Figure 7:
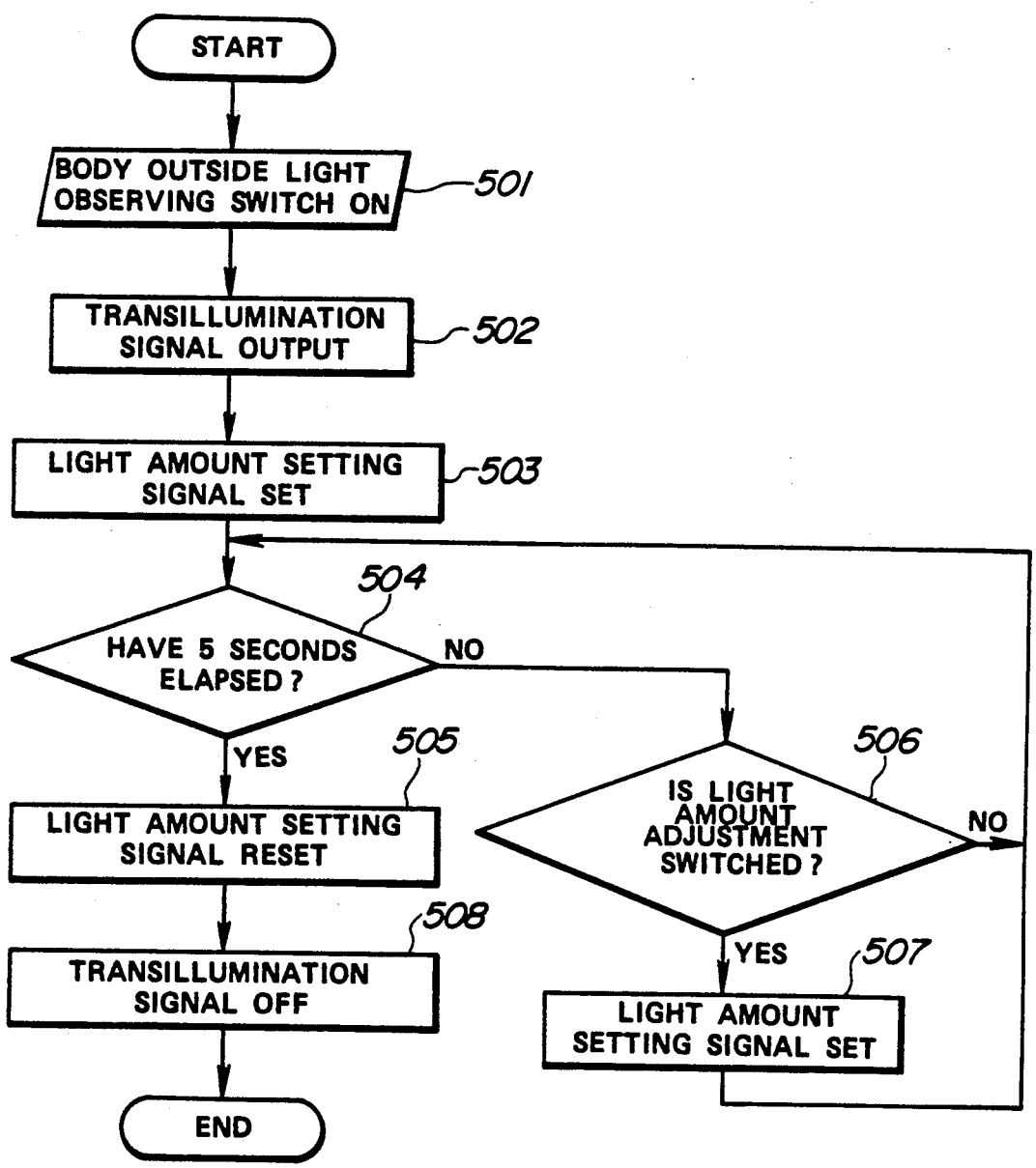

The operation of the CPU 39 shall be explained by using FIG. 7.

When, at 501, an on-signal is input from the body outside light observing switch 38, at 502, a transillumination signal will be generated and will be output to the motor movement controlling circuit 31, pulse light emission controlling circuit 41 and video signal processing circuit 37. Then, at 503, a light amount setting signal for setting the light amount is set and is output to the iris controlling circuit 48. At 504, whether 5 seconds have elapsed since the on-signal is input from the body outside light observing switch 38 is judged and, in case 5 seconds have elapsed, at 505, the light amount setting signal will be reset but, in case 5 seconds have not yet elapsed, at 506, whether the light amount adjusting switch 47 has been switched on will be judged. In case, at 506, the light amount adjusting switch 47 has been switched on, at 507, the light amount setting signal will be set but, in case it has not been switched on, the operation will return to 504.

When 5 seconds have elapsed, at 505, the light amount setting signal will be reset to make the light amount as before the transillumination is made. Then, at 508, the transillumination signal is switched off. When the transillumination signal is switched off, the motor movement controlling circuit 31 will move the rotary filter block 35 to insert the rotary filter 24 into the light path and the pulse light emission controlling circuit will resume the pulse light emission.

As the time when the light amount is increasing is automatically limited by the above operation, a burn will be prevented from occurring and, as the transillumination mode is automatically released, the trouble of releasing the transillumination mode will be omitted and the operatability will be high.

Figure 8:
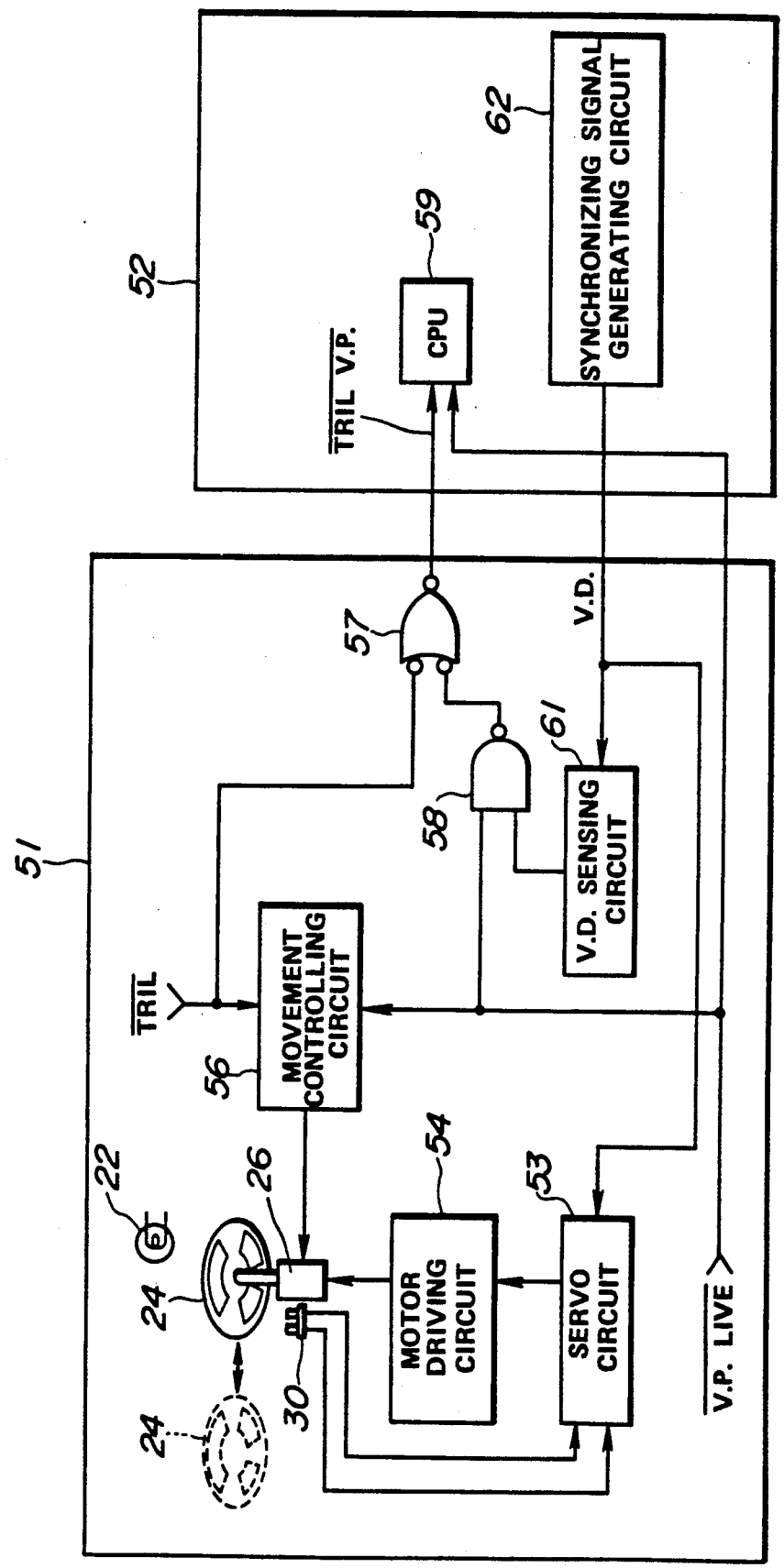

By the way, the signal may be transmitted between the video processor and light source apparatus as in FIG. 8.

In FIG. 8, a transillumination signal TRIL V.P and a mode sensing signal V.P. LIVE showing whether the endoscope connected to the light source apparatus is of an optical type or of an electronic type are transmitted to the video processor 52 from the light source apparatus 51.

In FIG. 8, the illuminating light emitted from the light source apparatus 22 within the light source apparatus 51 is transmitted through the rotary filter 24 and is sequentially separated into red (R), green (G) and blue (B). The rotary filter 24 is rotated and driven by the motor 26 and has the rotation detected by the photosensor 30 which outputs to the servo circuit 53 a timing signal which is synchronized with a synchronizing signal input from the video processor 52 and is output to the motor driving circuit 54. The motor driving circuit 54 rotates and drives the motor 26 from this signal.

In making a body outside light observation, the rotary filter 24, motor 26 and photosensor 30 are integrally retreated from the light path of the light source lamp 22 by the movement controlling circuit 56. The transillumination signal TRIL and mode sensing signal V.P. LIVE showing that the endoscope connected to the light source apparatus 51 is of an optical type may be input into the movement controlling circuit 56. In case either of them is input, the rotary filter 24 may be retreated from the light path as mentioned above.

Further, the transillumination signal TRIL is input into an AND gate 57 and the mode sensing signal V.P. LIVE is input into a NAND gate 58 and the CPU 59 within the video processor 52. A sensing signal is input into the NAND gate 58 from a V.D. sensing circuit 61 so that this V.D. sensing circuit 61 may generate the above mentioned V.D. sensing signal when the above mentioned synchronizing signal generated by the synchronizing signal generating circuit 62 within the video processor 52 is input.

The output of the above mentioned NAND gate 58 is input into the above mentioned AND gate 57. The output of the AND gate 57 is input into the above mentioned CPU 59.

In FIG. 8, when the body outside light observing switch 38 is switched on, the transillumination signal TRIL will be on the low level and will be input into one input terminal of the AND gate 57.

On the other hand, the H level mode sensing signal V.P. LIVE and H level V.D. sensing signal are input into the NAND gate 58 and the other input terminal of the AND gate 57 is on the L level so that the AND gate 57 may output the L level signal TRIL V.P to the CPU 59 and the CPU 59 may discriminate the transillumination.

Also, in case the optical endoscope is connected to the light source apparatus 51, the mode sensing signal V.P LIVE will be on the L level and will be input directly into the CPU 59. On the other hand, the output of the NAND gate 58 is on the H level and, as the transillumination signal TRIL is on the H level, the output signal TRIL V.P. of the AND gate 57 will be on the H level. When the mode sensing signal V.F. LIVE is on the L level, the CPU 59 will discriminate that the optical endoscope is connected.

Figure 9:
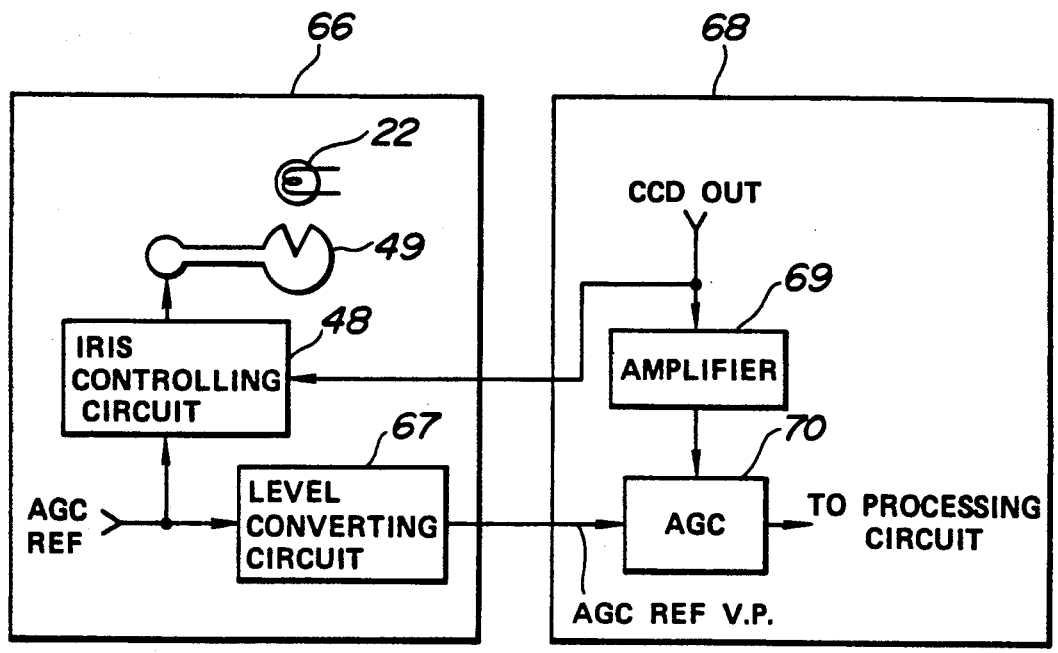

In FIG. 9, the iris 49 is operated with the reference value of an AGC circuit to control the light amount.

In FIG. 9, the light amount of the illuminating light output from the light source lamp 22 is adjusted by an iris 49. The reference value AGC REF of an AGC from a CPU not illustrated and the CCD output from a video processor 68 are input into the iris 49 so that the iris 49 may be controlled by the reference value AGC REF and CCD output.

The above mentioned reference value AGC REF is converted by a converting circuit 67 and is input into an AGC circuit 70 as an analogue signal AGC REF V.P. The CCD output amplified by the amplifier 69 is input into the AGC circuit 70, an AGC level is set by the analogue signal AGC REF V.P., has the gain adjusted and is output to a processing circuit not illustrated.

Figure 10:
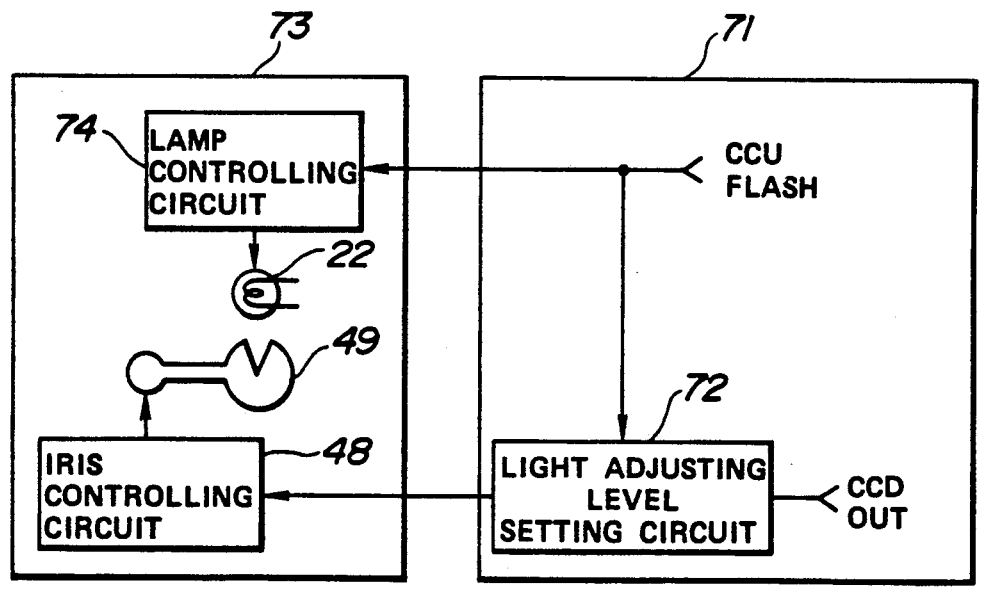

FIG. 10 is a diagram of a circuit having a device shutter mode.

In FIG. 10, a signal CCU FLASH showing a device shutter mode is input into a light adjusting level setting circuit 72 within a camera controlling unit (abbreviated as CCU hereinafter) 71 and into a lamp controlling circuit 74 within a light source apparatus 73 so that the iris 49 may be fully opened by the iris controlling circuit 48. When the signal CCU FLASH is input, the lamp controlling circuit 74 will emit a pulse light. Thereafter, the iris 49 operates to make the exposure amount proper and the device shutter is driven.

Figure 11:
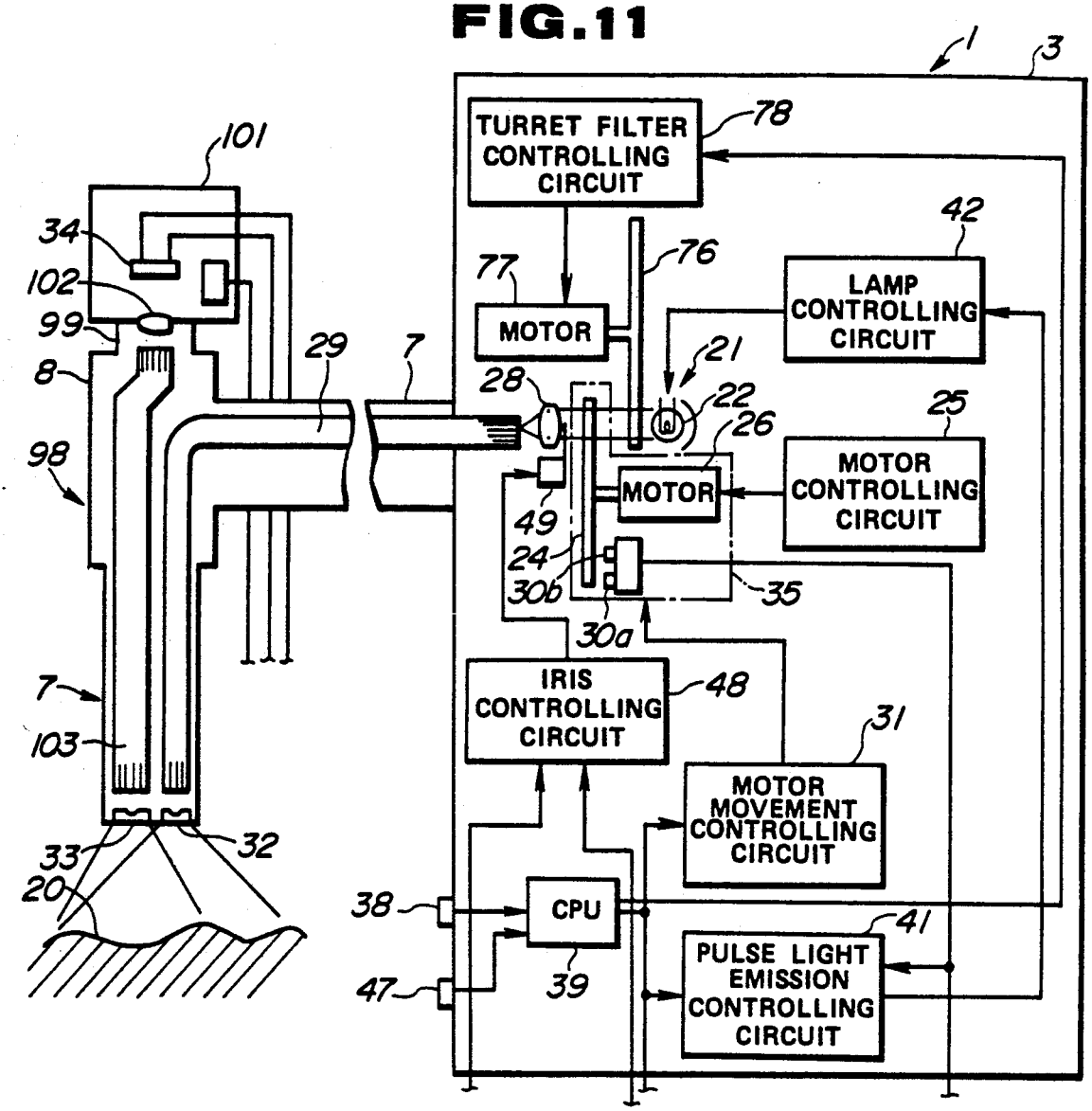
FIGS. 11 to 13 relate to the second embodiment of the present invention.
Figure 12:
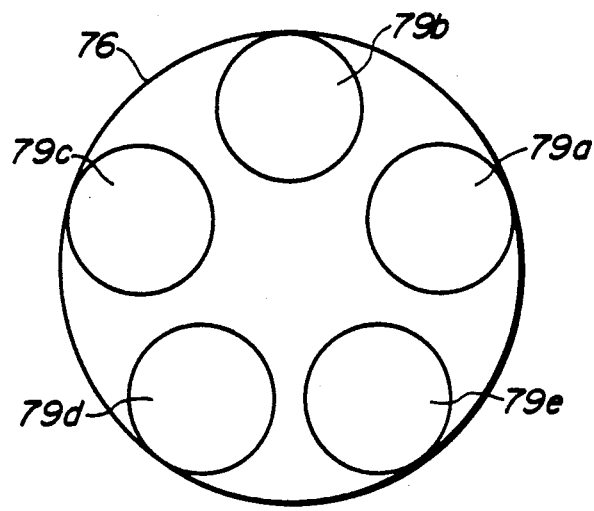
Figure 13:
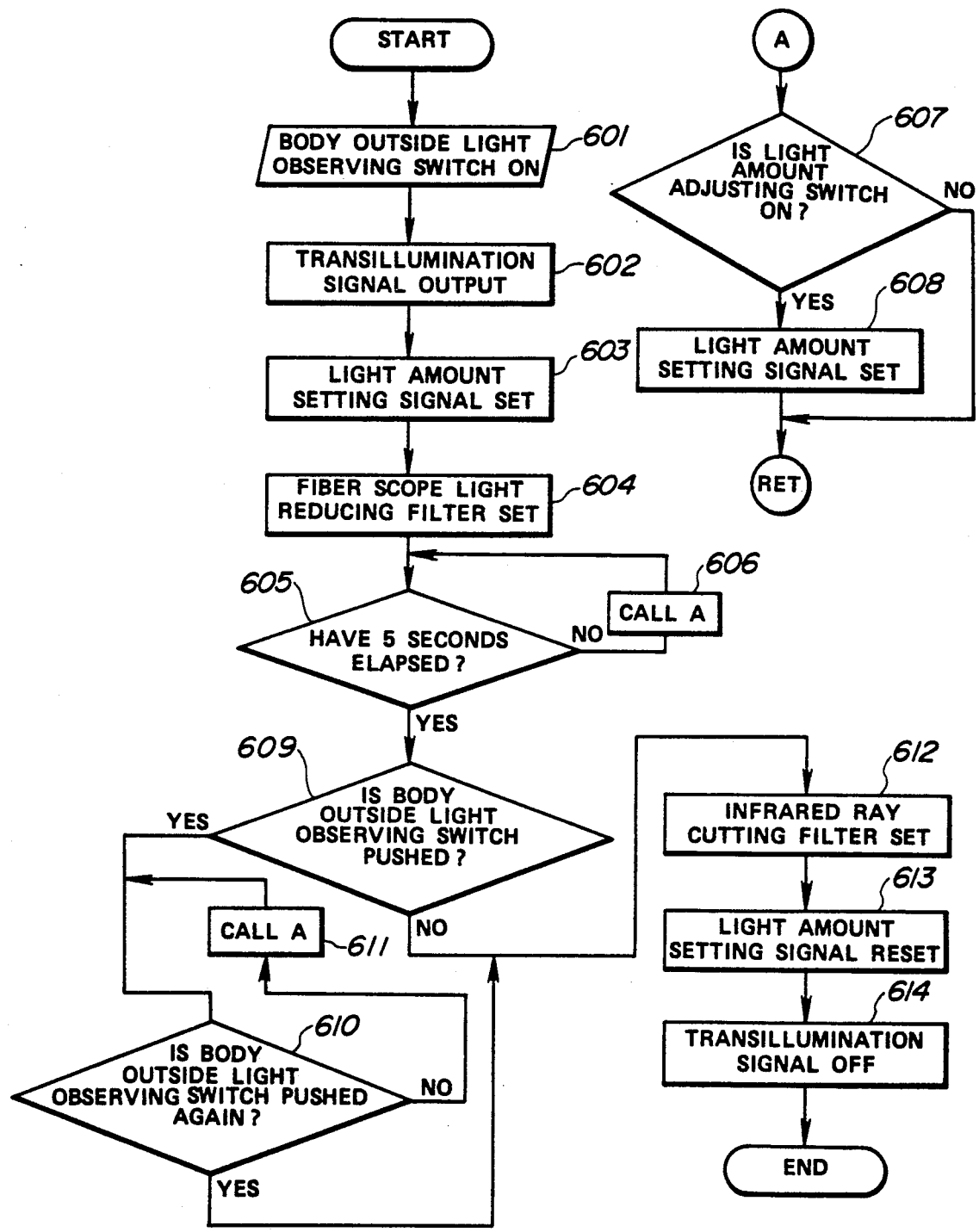

FIGS. 11 to 13 show the second embodiment of the present invention.

This embodiment can be used not only as combined with a frame sequential type controlling apparatus but also as a light source for a conventional optical endoscope (fiber scope).

By the way, this embodiment is the same as the first embodiment except having a turret filter 76, a motor 77 for rotating and driving this turret filter 76 and a turret filter controlling circuit 78 for controlling this motor. The same formations shall bear the same respective reference numerals and shall not be explained.

The light source apparatus 3 of this embodiment has the turret filter 76 arranged in the light path of the light source lamp 22 and the turret filter controlling circuit 78. As shown in FIG. 12, the turret filter 76 is provided in the peripheral direction with an infrared ray cutting filter 79a to be arranged in the light path in case the light source is used as a frame sequential light source, a fiber scope light reducing filter 79b to be arranged in the light path in case it is used as a fiber scope light source, a universal filter 79c which can be freely replaced and used by the operator, a rigid scope light reducing filter 79d to be arranged in the light path in case the light source is used as a rigid scope light source and an emergency light 79e.

By the way, a fiber scope 98 connected to the light source apparatus 3 is removably fitted with an externally fitted television camera 101 in an eyepiece part 99 provided at the rear end of the operating part 8. A light distributing lens system 32 and objective lens system 33 are provided in the tip part of the insertable part 7. The entrance end surface of an image guide 103 is provided in the rear of the objective lens system 33. An object image is formed on this entrance end surface by the objective lens system 33 and this optical image is transmitted through the image guide 103 to the above mentioned eyepiece part 99. Further, the optical image is formed on the imaging surface of a CCD 34 within the externally fitted television camera 101 by an eyepiece lens system 102 provided in the eyepiece part 99.

The above mentioned CCD 34 is connected to the video signal processing circuit 37 of the controlling apparatus 4 so that the electric signal output from the CCD 34 may be processed to be a standard video signal which is output to the monitor 6.

The operation shall be explained with the flow chart in FIG. 13.

When, at 601, an on-signal is input into the CPU 39 from the body outside light observing switch 38, at 602, a transillumination signal will be output to the motor movement controlling circuit 31, pulse light emission controlling circuit 41 and video signal processing circuit 37. At 603, a light amount setting signal is output so as to set the iris 49 in a proper position with respect to the iris controlling circuit 48. At 604, an instruction is issued to insert the fiber scope light reducing filter 79b into the light path in order to prevent the light guide 29 from being burned by the increase of the light amount. The CPU 39 has a timer, for example, of 5 seconds the same as in the first embodiment. AT 605, it is judged whether 5 seconds have elapsed. In case 5 seconds have elapsed, the operation will move to 609 but, in case 5 seconds have not elapsed, the operation will shift to 606. At 606, it is judged whether, at 607, the light amount adjusting switch 47 is switched on as in FIG. 13(b). In case it is on, at 608, a light amount setting signal will be set and the operation will return to 605 but, in case it is not on, the operation will return to 605. After 5 seconds have elapsed, at 609, it is judged whether the body outside light observing switch 38 is pushed. In case it is pushed, the operation will shift to 610 but, in case it is not pushed, the operation will shift to 612. At 610, it is judged whether the body outside light observing switch is pushed again. In case it is not pushed turning in the flow in FIG. 13(b), the body outside light observation will be continued. In case the switch 38 is pushed, the operation will shift to 612. At 612 the infrared ray cutting filter 79a is inserted into the light path. At 613, the light amount setting signal is reset and then, at 614, the transillumination signal is switched off.

By the way, when the infrared ray cutting filter 79a and fiber scope light reducing filter 79b are arranged adjacently to each other, the turret filter 76 switching time will be able to be reduced.

According to this embodiment, in case the turret filter 76 is provided and a body outside light observation is made, as the fiber scope light reducing filter 79b is inserted, the light guide 29 will be able to be prevented from being burned.

The other effects are the same as in the first embodiment.

By the way, such transillumination signal TRIL V.P and mode sensing signal V.P. LIVE as are described in FIG. 6 may be input into the CPU 39 to control the turret filter.

Figure 14:
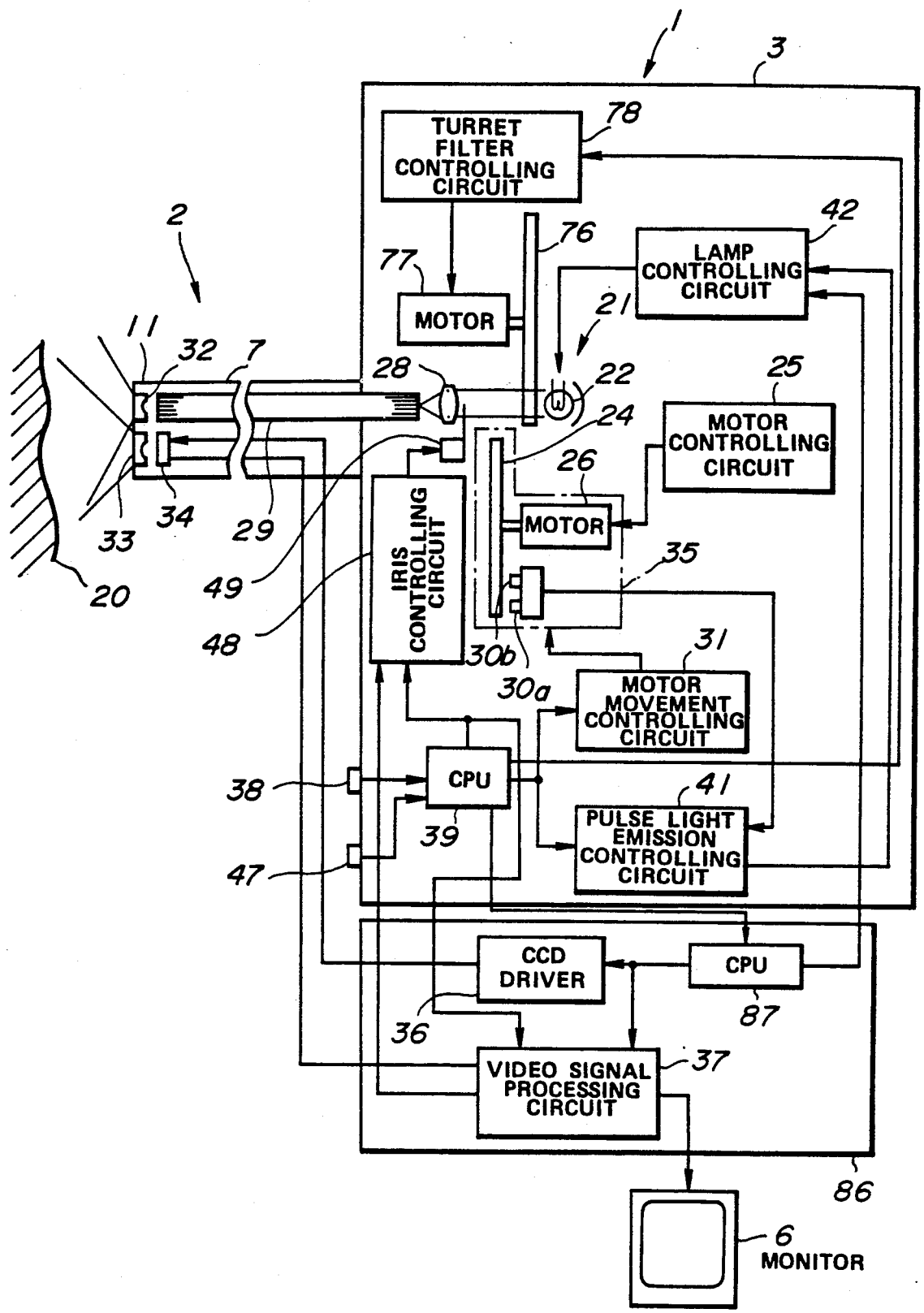
FIG. 14 relates to the third embodiment of the present invention and is a block diagram showing the general formation of an electronic endoscope.

FIG. 14 shows the third embodiment of the present invention.

This embodiment is a combination of the simultaneous type controlling apparatus 86 corresponding to the simultaneous type CCD and the light apparatus 3 described in the second embodiment with each other. The simultaneous type CCD has a device shutter mode which can reduce the exposure accumulating time to obtain a still image having no movement. Even in the endoscope, that operation is effective but, if the device shutter mode is always used, as the emitted light must be increased, there will be a danger of causing a burn. If the device shutter is used only in the case of stilling the image, a favorable observation will be able to be made.

The above mentioned still image is displayed as in the following.

When a freezing signal for stilling an image is output from the CPU 87, this signal will be input into the CCD driver 36 and video signal processing circuit 37 and the CCD 34 will be of a device shutter mode. At the same time, a flash instructing signal will be input into the lamp controlling circuit 42 from the CPU 87, the light source lamp 22 will flash and the emitted light will increase. The iris controlling circuit 48 adjusts the light amount with an EE signal from the video signal processing circuit 37. In case the CCD 34 becomes of a proper exposure, freezing will be made by the video signal processing circuit 37.

The device shutter mode requires an increase of the light amount as mentioned above and therefore is used only in freezing but can be used in the body outside light observation. When the body outside light observing switch 38 is pushed, the CPU 39 will instruct the controlling circuit 48 to fully open the iris 49 and will output to the lamp controlling circuit 42 a signal to increase the light amount and also the output of the CPU 39 will be transmitted to the CPU 87 of the simultaneous type controlling apparatus 86 to inform of the body outside observing mode. On the basis of this signal, the CPU 87 outputs a signal to the video signal processing circuit 87 so that the CCD driver 36 may be of a device shutter mode. The output signal of the video signal processing circuit 37 is transmitted to the CCD driver 36 so that the exposure amount may be constant to determine the shutter time of the device shutter mode. The operation of the body outside light observing mode is substantially the same as in the first embodiment except that there is no rotary color filter 24 so that, when the time, for example, of 5 seconds has elapsed since the body outside light observing switch 38 is pushed, the emitted light amount of the lamp 22 will be returned to the ordinary amount, the device shutter mode will be released and the iris 49 will return to the proper position.

According to this embodiment, even in the combination with the simultaneous type controlling apparatus 86, during the body outside light observing mode, the light amount can be increased for a fixed time, the position of the scope tip part can be known from the scope emitted light leaking outside the body and further a normal image can be obtained on the monitor 6 by using the device shutter mode in combination.

The other effects are the same as in the first embodiment.

Figure 15:
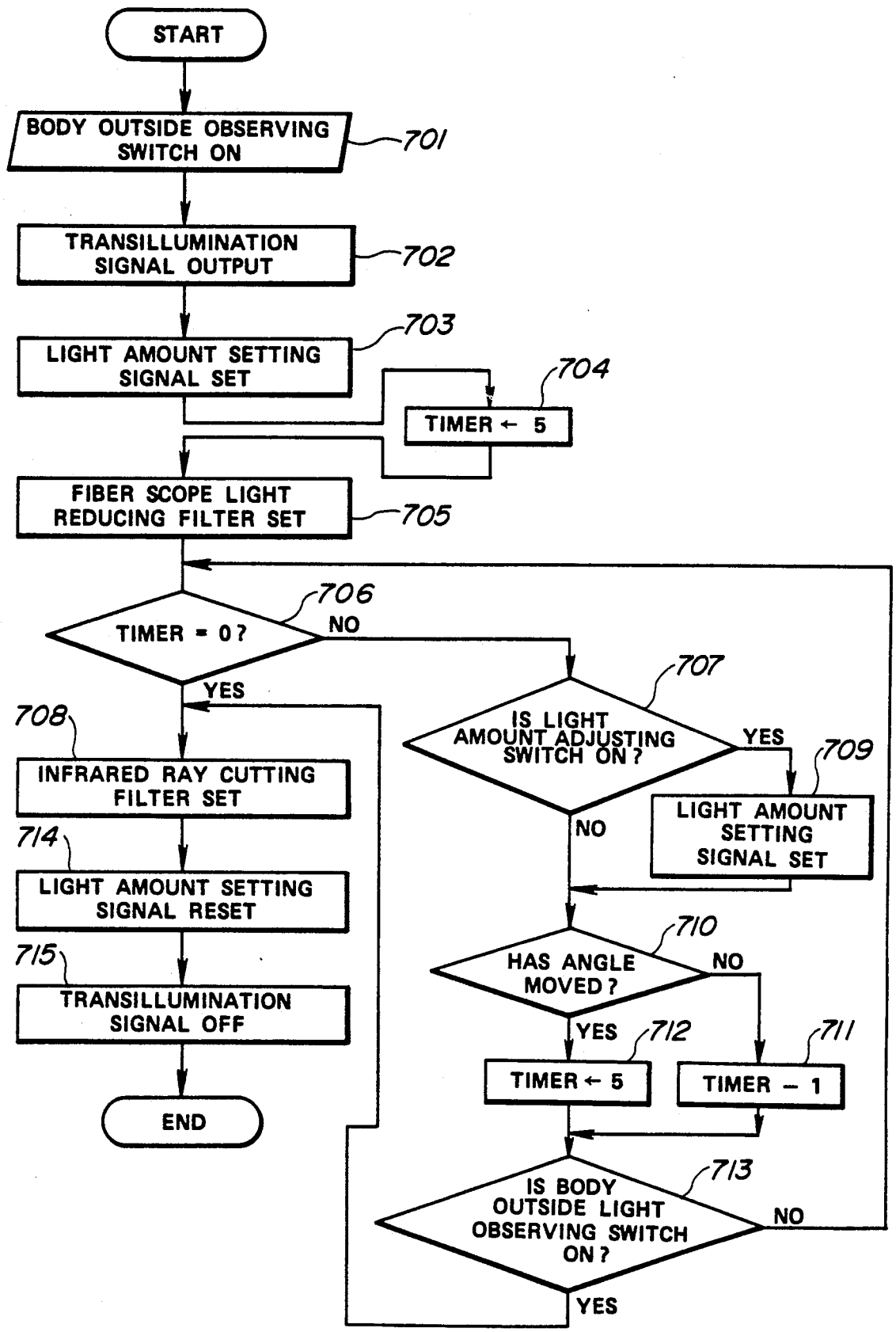
FIG. 15 relates to the fourth embodiment of the present invention and is a flow chart for explaining the operation.

FIG. 15 shows the fourth embodiment of the present invention.

In this embodiment, the CPU 39 of the light source apparatus 3 monitors the movement of the curving operation knob 14 with a sensor provided in the operating part 8 of the endoscope 2 so that, in case the knob moves, the time for the body outside light observation may be extended.

In FIG. 15, when, at 701, the body outside light observing switch 38 is switched on, at 702, the CPU 39 will output a transillumination signal and, at 703, a light amount setting signal will be set. At 704, 5 is input into the timer and then, at 705, the fiber scope light reducing filter 79b is inserted into the light path. At 706, whether the timer indicates 0 or not is judged. In case the timer indicates 0, the operation will shift to 708 but, in case the timer does not indicate 0, the operation will shift to 707. At 707, whether the light amount adjusting switch 47 is on or not is judged. In case it is on, the operation will shift to 709 but, in case it is not on, the operation will shift to 710. At 709, the light amount setting signal is set and the operation shifts to 710. At 710, it is judged whether the angle of the curvable part 12 has moved or not, that is, whether the curving operation knob 14 shown in FIG. 3 has been operated. In case the angle has moved, there will be no danger of a burn and therefore, at 712, 5 is again input into the timer. In case the angle has not moved, at 711, 1 is subtracted from the value shown in the timer. At 713, it is judged whether the body outside light observing switch 38 is on. In case it is not on, the operation will shift to 706 but, in case it is on, the operation will shift to 708. At 708, the infrared ray cutting filter 79a is inserted into the light path. At 714 the light amount setting signal is reset. Thereafter, the transillumination signal is switched off.

In this embodiment, as the danger of causing a burn is automatically sensed and the transillumination is released, so long as there is no danger of a burn, the transillumination mode can be continued for a long time.

Figure 16A:
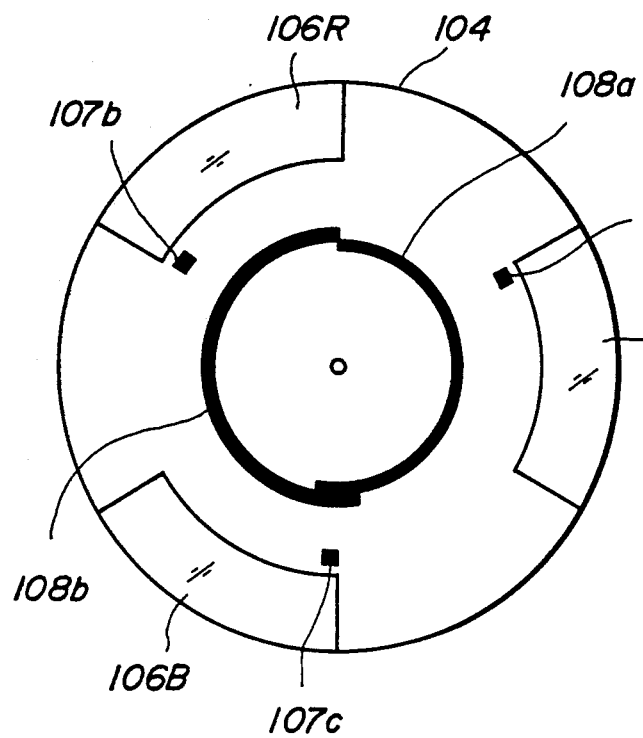
FIGS. 16 and 17 relate to the fifth embodiment of the present invention.
Figure 16B:
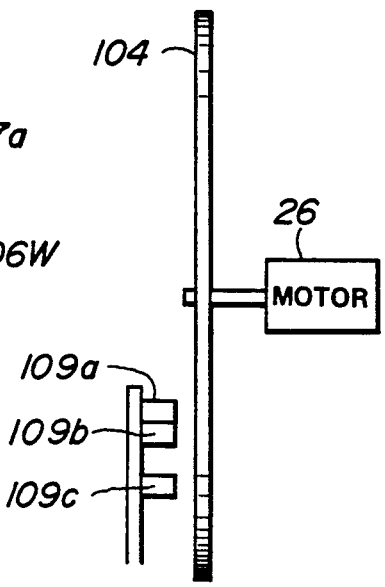
Figure 17:
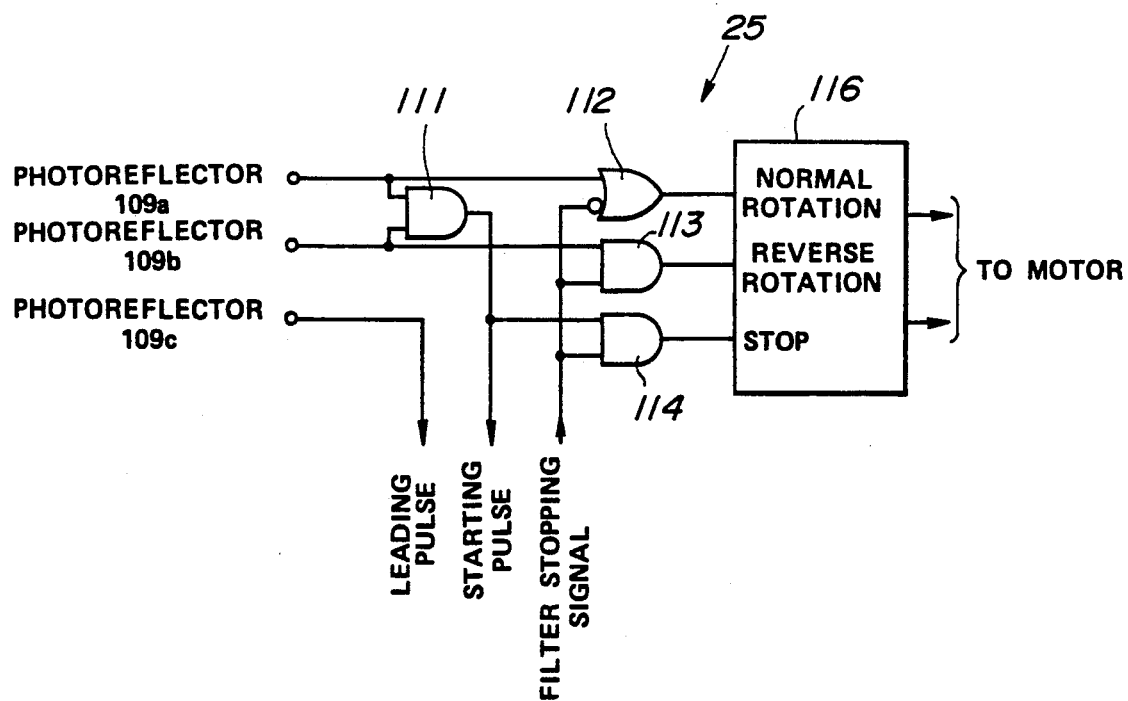

FIGS. 16 and 17 show the fifth embodiment of the present invention.

In this embodiment, by making the frame sequential illuminating light in R, W (white color) and B instead of R, G and B, the frame sequential type light source and white color light source can be used in common so that, in the case of the body outside light observing mode, the white color light may be fed to the endoscope.

A rotary color filter 104 shown in FIG. 16(a) is provided in the light source part 21 of the light source apparatus 3 of this embodiment. This rotary color filter 104 is provided peripherally with a color transmitting filter 106R transmitting a red (R) color, a color transmitting filter 106W transmitting a white (W) color light and a color transmitting filter 106B transmitting a blue (B) color.

There are arcuately provided starting marks 107a, 107b and 107c on the inside diameter sides of the color transmitting filters 106R, 106W and 106B and further marks 108a and 108b on the inside diameter sides of the starting marks 107a, 107b and 107c.

Photoreflectors 109a, 109b and 109c are provided as opposed to the above mentioned marks 107a, 107b, 107c, 108a and 108b so that which filter of the color transmitting filters 106R, 106W and 106B is inserted in the light path connecting the entrance end surface of the light guide 29 and the light source lamp 22 may be discriminated.

The above mentioned rotary color filter 104 is controlled in rotation by a motor controlling circuit 25 shown in FIG. 17.

In FIG. 17, signals from the photoreflectors 109a, 109b and 109c are input into the motor controlling circuit 25. The photoreflector 109a is connected to one input end of an AND gate 111 and one input end of an OR gate 112. The photoreflector 109b is connected to the other input end of the above mentioned AND gate 111 and one input end of an AND gate 113. The photoreflector 109c is connected to a pulse light emission controlling circuit 41 and outputs a leading pulse. The output end of the AND gate 111 is connected to the above mentioned pulse light emission controlling circuit 41 and one input end of the AND gate 114 and outputs a starting pulse to the pulse light emission controlling circuit 41.

A reversed filter stopping signal, that is, a transillumination signal is input into the other input end of the above mentioned OR gate 112 from the CPU 39. Further, a filter stopping signal is input into the other ends of the above mentioned AND gates 113 and 114. The output end of the OR gate 112 is connected to the normal rotation terminal of a motor controller 116. The output end of the AND gate 113 is connected to the reverse rotation terminal of the motor controller 116. The output end of the AND gate 114 is connected to the stopping terminal of the motor controller 116.

In this embodiment formed as mentioned above, in the case of an ordinary observation, the transillumination signal, that is, the filter stopping signal will be on the L level and the outputs of the photoreflectors 109a and 109b will be on the H or L level but only the OR gate 112 will be on the H level and the outputs of the other AND gates 113 and 114 will be on the L level. Therefore, only the normal rotation terminal of the motor controller 116 will be on the H level and the motor controller 116 will rotate and drive the rotary color filter 24.

Now, when an on-signal is input into the CPU 39 from the body outside light observing switch 38, the CPU 39 will output a transilluminatin signal, that is, a filter stopping signal to the motor controlling circuit 25 so that the other input end of the OR gate may be on the L level and the other input ends of the AND gates 113 and 114 may be on the H level. In this case, if the mark 108a is detected by the photoreflector 109a, one input end of the AND gate 111 and one input end of the OR gate 112 will be on the H level and the OR gate 112 will output an H level signal to the normal rotation terminal of the motor controller 116. Also, in case the photoreflector 109a outputs an H level signal, the output of the photoreflector 109 will be on the L level and therefore the other input end of the AND gate 111 will be on the L level and will output an L level signal. This L level signal will be output to the AND gate 114, the output of the AND gate 114 will be on the L level and the stopping terminal of the motor controller 116 will be on the L level. Further, the AND gate 113 will receive the L level signal from the photoreflector 109b and will output an L level signal and the reverse rotation terminal of the motor controller 116 will be on the L level.

Thus, in case the mark 108a is detected by the photoreflector 109a, the rotary color filter 24 will make a normal rotation.

Also, when the mark 108b is detected by the photoreflector 109b, only the reverse rotation terminal of the motor controller 116 will be on the H level, the others will be on the L level and therefore the rotary color filter 24 will reversely rotate.

Further, when the color transmitting filter 106W transmitting a white color light is inserted into the light path, the overlapped parts of the marks 108a and 108b will be positioned to be opposed to the photoreflectors 109a and 109b which will output H level signals. When the outputs of the photoreflectors 109a and 109b are on the H level, the outputs of the OR gate 112 and AND gates 113 and 114 will be also on the H level. In this case, the motor controller 116 will preferentially receive the H level of the stopping terminal and will stop the rotary color filter 24. Thereby, the color transmitting filter 106W of the rotary color filter 24 will stop in the light path and the white color light transmitted through this color transmitting filter 106W will be fed to the endoscope 2.

The color transmitting filter 106W can feed a large light amount to the endoscope 2 without limiting the wavelength band of the transmitted illuminating light as in the other color transmitting filters 106R and 106B.

After, for example, 5 seconds have elapsed, the CPU 39 will have the filter stopping signal on the L level. Thereby, the OR gate 112 will be on the H level, the AND gates 113 and 114 will be on the L level and the motor controller 116 will normally rotate the rotary color filter 24.

In this embodiment, at the time of the body outside light observing mode, the color transmitting filter 106W transmitting a white color light may be inserted into the light path to increase the light amount of the illuminating light. As a rotary color filter 24 moving mechanism is not provided, the light source apparatus 3 can be made small.

The other formations, operations and effects are the same as in the first embodiment.

FIG. 18 shows the sixth embodiment of the present invention.

In this embodiment, the rotary color filter 24 is not moved but is detoured by using mirrors.

The light source part 21 of this embodiment is not provided with the rotary filter block 35 and motor movement controlling circuit 31 described in the first embodiment.

As shown in FIG. 18, a light source part 21 of this embodiment comprises a light source lamp 22 emitting a white color light, a rotary color filter 24, a condenser lens 28, rotary mirrors 120a and 120b and mirrors 121a and 121b so that the white color light from the light source lamp 22 may be fed to the condenser lens 28 without being transmitted through the above mentioned color transmitting filters 23R, 23G and 23B.

The above mentioned rotary mirrors 120a and 120b have respectively pinions 123a and 123b meshed with a rack 122 which is further meshed with a pinion 125 provided on a rotary mirror motor 124 driving shaft and is arranged to transmit the rotation of the rotary mirror motor 124 to the rotary mirrors 120a and 120b.

Figure 18A:
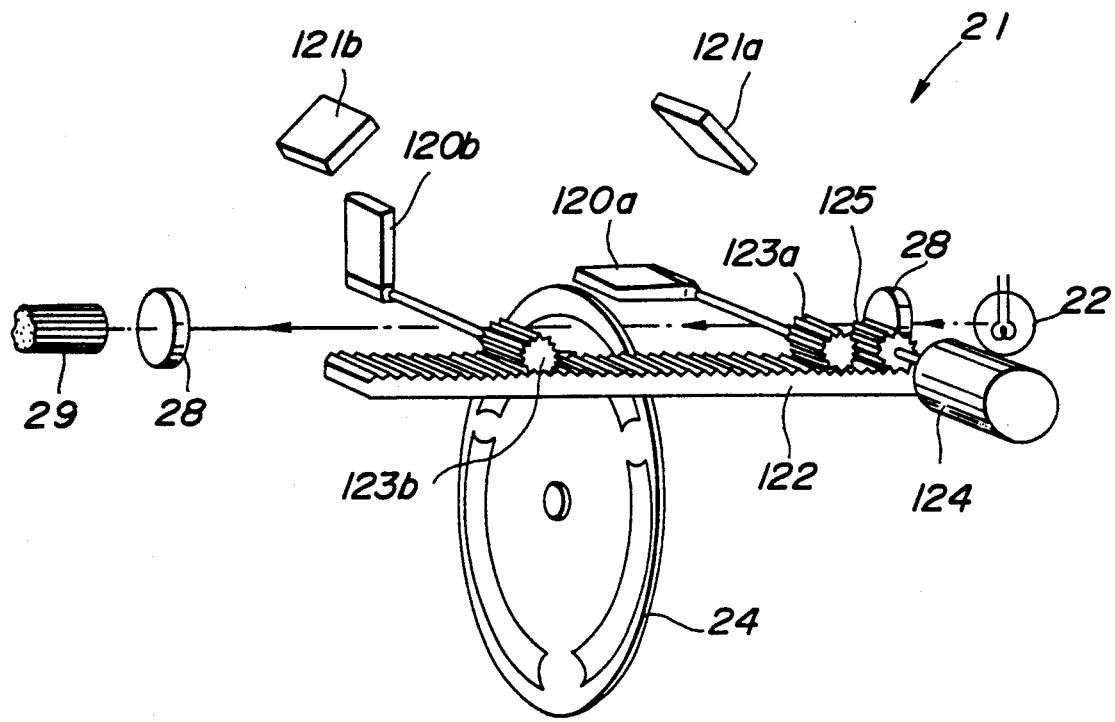
FIG. 18 relates to the sixth embodiment of the present invention and is an explanatory view of the formation of a light source part.
Figure 18B:
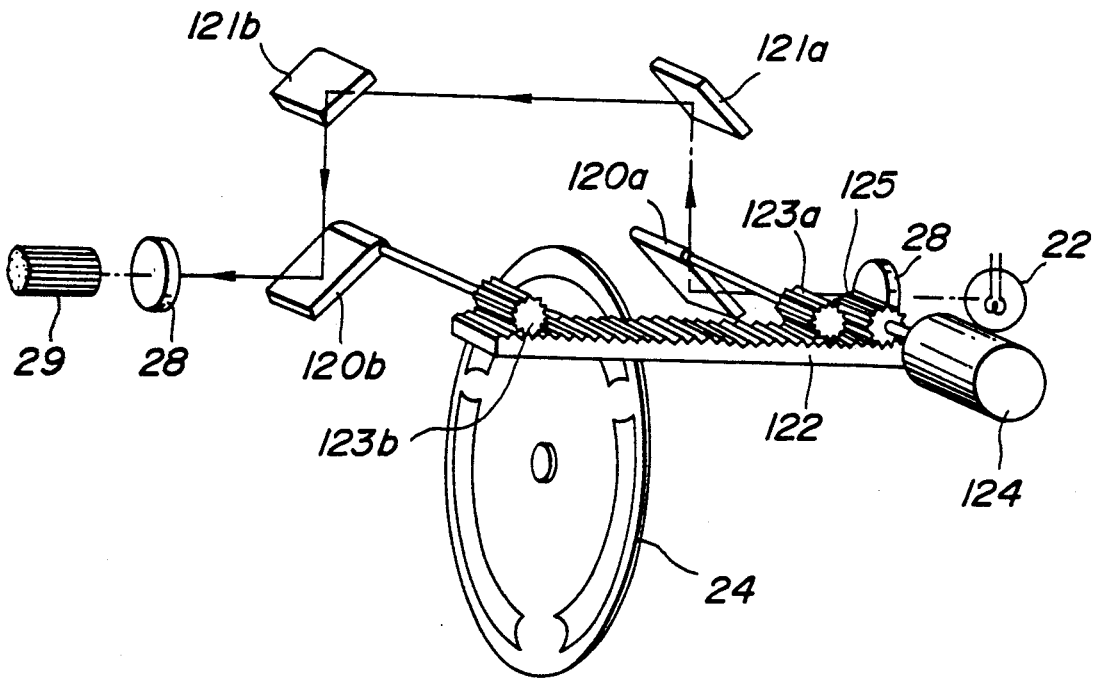

In the light source part 21 formed as mentioned above, by an on-signal from the body outside light observing switch 38, the CPU 39 outputs a transillumination signal which is output to a motor controlling circuit which drives a rotary mirror motor 124. When the motor 124 is driven, as shown in FIG. 18(b), the rotary mirror 120a will stop in the position in which the entrance angle of the white color light is 45 degrees and the rotary mirror 120b will stop in the position in which the reflecting surface makes an angle of 45 degrees with the light path connecting the light source lamp 22 and condenser lens 28. The mirrors 121a and 121b are provided respectively at an angle of 45 degrees with the light path from the light source lamp 22 to the condenser lens 28 and are arranged so that the reflected light from the rotary mirror 120a may be injected at an injection angle of 45 degrees into the rotary mirror 120b to feed a white color light to the entrance end surface of the light guide 29.

When, for example, 5 seconds have elapsed in a built-in timer not illustrated, the CPU 39 will stop the output of the transillumination signal and thereby a motor controlling circuit not illustrated will instruct the rotation of the rotary mirror motor 124. As shown in FIG. 18(a), the rotary mirrors 120a and 120b will retreat from the light path from the light source lamp 22 to the condenser lens 28 and the white color light will be made illuminating lights of the respective wavelengths of R, G and B sequentially by the rotary filter 24.

The other formations are the same as in the first embodiment.

This embodiment has the same effects as of the first embodiment.

Figure 19:
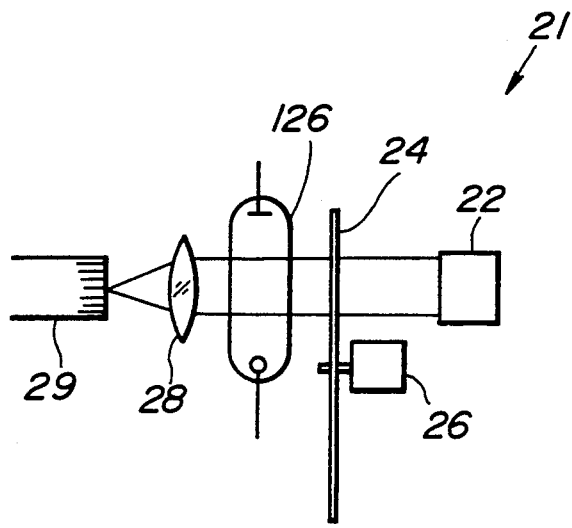
FIG. 19 relates to the seventh embodiment of the present invention and is an explanatory view of a light source part.

FIG. 19 shows the seventh embodiment of the present invention.

This embodiment is provided with a transillumination lamp in the light source part.

In this embodiment, a strobe tube 126 is provided between the rotary color filter 24 and condenser lens 28 and in the light path.

In this embodiment, when an on-signal is input from the body outside light observing switch 38, the CPU 39 will start the pulse light emission of the strobe tube 126. The light emitted from the strobe tube 126 is added together with the light output from the light source lamp 22 to be increased in the light amount and is radiated to the entrance end surface of the light guide 29.

The other formations and operations are the same as in the first embodiment.

In this embodiment, as there is no moving means for moving the rotary color filter 24, the mechanism can be simplified and the rate of generation of troubles can be made low.

Figure 20:
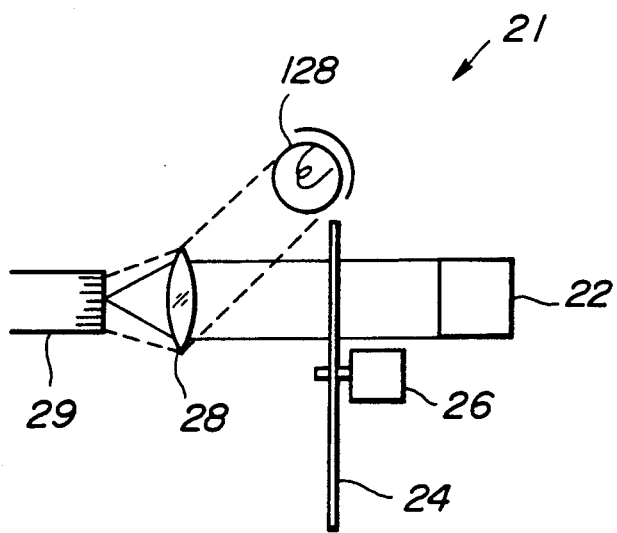
FIG. 20 relates to the eighth embodiment of the present invention and is an explanatory view of a light source part.

FIG. 20 shows the eighth embodiment of the present invention.

This embodiment is provided with a transillumination lamp the same as in the seventh embodiment but is different from the seventh embodiment in respect that this transillumination lamp is provided outside the light path.

In the light source part 21 of this embodiment, an auxiliary lamp 128 is provided off the light path connecting the light guide 29 and light source lamp 22 so that the light output from this auxiliary lamp 128 may enter the condenser lens 28 to be radiated to the entrance end surface of the light guide 29.

In this embodiment, when a transillumination signal is output from the CPU 39, the auxiliary lamp 128 will light. Then, the illuminating light output from the auxiliary lamp 128 will be added to the illuminating light output from the light source lamp 22 to increase the light amount and this increased light will be fed to the endoscope.

By the way, the auxiliary lamp 128 may be made an emergency light.

The other formations, operations and effects are the same as in the first embodiment.

Figure 21:
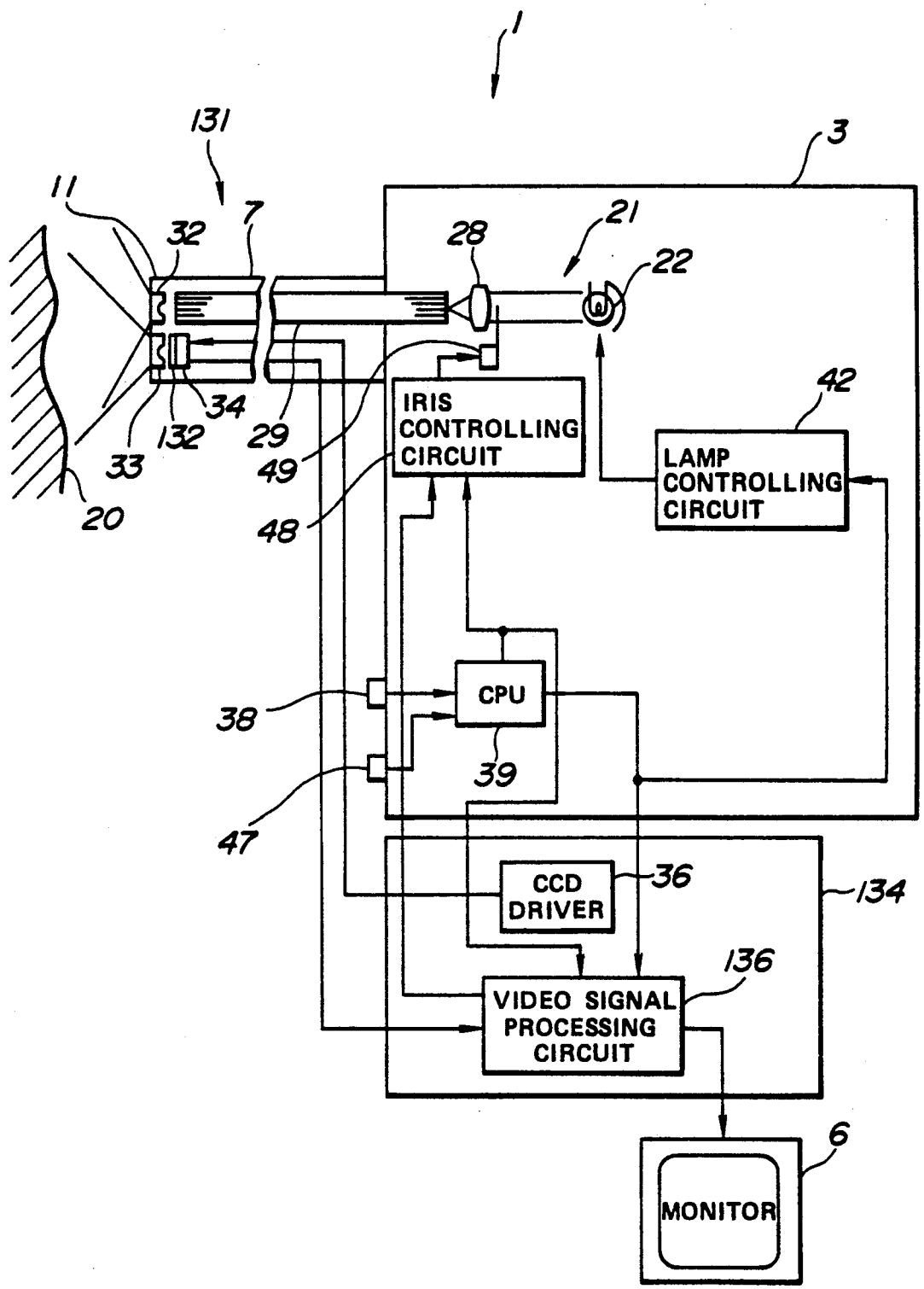
FIGS. 21 and 22 relate to the ninth embodiment of the present invention.
Figure 22:
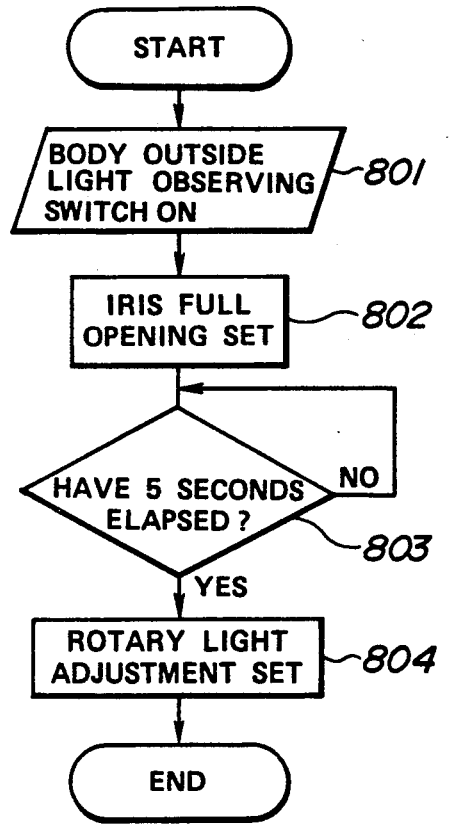

FIGS. 21 and 22 show the ninth embodiment of the present invention FIG. 21 is a block diagram showing the general formation of an electronic endoscope apparatus.

In this embodiment, the present invention is applied to a simultaneous type electronic endoscope apparatus.

In this embodiment, only the differences from the frame sequential type electronic endoscope apparatus in FIG. 2 shall be explained.

A color mosaic filter 132 is provided on the imaging surface of the CCD 34 of an endoscope 131 of this embodiment so as to color-separate the light returning from the object.

In a light source apparatus 133, there are omitted the rotary filter block 35, motor controlling circuit 25, motor movement controlling circuit 31 and pulse light emission controlling circuit 41 shown in FIG. 2.

Further, a simultaneous type video signal processing circuit 136 is provided within the controlling apparatus 134 so as to process the electric signal from the above mentioned CCD 34.

The CPU 39 of the light source apparatus 3 formed as mentioned above operates as in FIG. 22.

When, at 801, the body outside light observing switch 38 is switched on, at 802, a control signal will be output to the iris controlling circuit 48 to fully open the iris 49. Thereby, the iris 49 is fully opened. Then, at 803, it is judged whether 5 seconds have elapsed or not since the iris 49 is fully opened. In case 5 seconds have not yet elapsed, the operation will return to 803 but, in case 5 seconds have elapsed, the operation will proceed to 804. At 804, a control signal is output to the iris controlling circuit 48 to again make an automatic light adjustment. Thereby, the light amount becomes to be of a proper value and the transillumination ends.

Even in a simultaneous type endoscope, in case the distance between the body cavity inside wall 20 and the endoscope tip part is short, the light emitted from the endoscope tip part by the automatic light adjustment will be reduced. Therefore, even with the simultaneous type, the position of the endoscope tip part may not be sensed from outside the body In such case, in this embodiment, when the body outside light observing mode is made, the iris 49 will be fully opened to increase the light amount of the illuminating light fed to the endoscope 131 and therefore the endoscope tip part will be able to be sensed with the body outside transmitted light.

The other formations and operations are the same as in the first embodiment.

This embodiment has the same effects as in the first embodiment.

Figure 23:
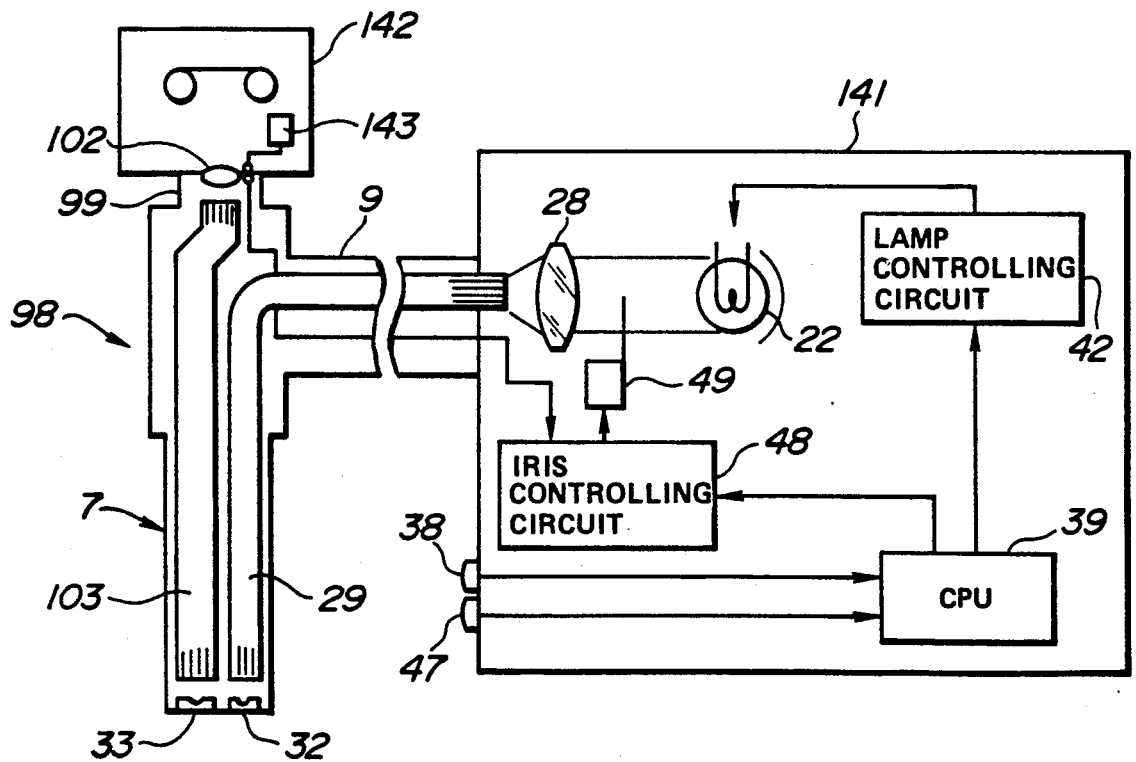

FIGS. 23 to 25 show the tenth embodiment of the present invention.

In this embodiment, the present invention is applied to a fiber scope light source apparatus 141.

An endoscope camera 142 is removably connected to an eyepiece part 99 of a fiber scope 98 of this embodiment. A light measuring circuit 143 is provided within the endoscope camera 142 so that an EE signal output from the light measuring circuit 143 may be input into the iris controlling circuit 48 within the light source apparatus 141 through the operating part 8 and light guide and signal cable 9 of the fiber scope 98.

The CPU 39 provided within the light source apparatus 141 operates as shown in FIG. 24.

In FIG. 24, when, at 901, the body outside light observing switch 38 is set on, at 902, a control signal will be output to the controlling circuit 48 to fully open the iris 49. The iris 49 is thereby fully opened. At 903, a control signal is output to the lamp controlling circuit 42 to increase the light amount. The light source lamp 22 increases the light amount of the illuminating light emitted thereby. At 904, it is judged whether 5 seconds have elapsed or not since the lamp light amount is increased. In case 5 seconds have not elapsed, the operation will return to 904 but, in case 5 seconds have elapsed, the operation will proceed to 905. At 905, a control signal is output to the lamp controlling circuit 42 to reduce the light amount of the light source lamp 22 and the light amount output by the light source lamp 22 is reduced. Then, at 906, a control signal is output to the iris controlling circuit 48 to automatically adjust the light. Thereby, the illuminating light fed to the fiber scope 98 becomes to be of a proper value and the transillumination ends.

By the way, in the case of the body outside light observing mode, when not only the light amount is increased to be of a fixed value as shown in FIG. 25(a) but also a pulse light is emitted as in FIG. 25(b), the endoscope tip part will be able to be more easily confirmed.

In such apparatus using the fiber scope 98 as in this embodiment, the light amount of the illuminating light emitted from the endoscope tip part is controlled by an EE signal from the endoscope camera 142. Therefore, at the time of a near focus observation, the light will be reduced by the iris 49 to be so little that the position of the endoscope tip part may not be confirmed from outside the body. In such case, in this embodiment, the iris 49 will be fully opened to further increase the light amount so that the endoscope tip part may be confirmed.

As explained above, according to the present invention, as the increase of the light amount by the transillumination is automatically released, a burn can be prevented from being generated by the observing light.

What is claimed is:

1. An endoscope apparatus comprising:
an endoscope provided with an insertable part tip part to be inserted into a body cavity and having an observing window for observing an object to be imaged and an illuminating window for emitting an illuminating light to illuminate said object;
a light source apparatus including an illuminating light feeding means for generating an illuminating light to be fed to said endoscope and a light amount increasing means for increasing for a preset time the light amount of the illuminating light generated by said illuminating light feeding means when a body outside light observing signal is input for confirming from outside the body a position within the body cavity of said endoscope tip part; and a body outside light observing signal generating means for generating said body outside light observing signal.

2. An endoscope apparatus according to claim 1 wherein said illuminating light feeding means comprises a light source lamp for generating said illuminating light, a lamp controlling means for feeding electric power to said light source lamp and a rotary filter inserted into a light path of the illuminating light output from said light source lamp for separating said illuminating light into color lights for color-photographing.

3. An endoscope apparatus according to claim 2 wherein said light amount increasing means comprises a filter moving means for retreating said rotary filter means from the light path when said body outside light observing signal is input and an iris means for adjusting illuminating light output from said illuminating light feeding means.

4. An endoscope apparatus according to claim 3 wherein said light mount increasing means further comprises a turret means comprising at least a filter for reducing the light amount of the illuminating light generated by said illuminating light feeding means and an infrared ray cutting filter for removing an infrared ray component of said illuminating light.

5. An endoscope apparatus according to claim 2 wherein said rotary filter means has red, green and blue color separating filters for separating the illuminating light into color lights for color-photographing.

6. An endoscope apparatus according to claim 2 wherein said rotary filter means has red and blue color separating filters for separating the illuminating light into color lights for color-photographing and filter for transmitting a white color light.

7. An endoscope apparatus according to claim 6 wherein said illuminating light feeding means further has a controlling circuit for positioning said white color light transmitting filter in the light path when said body outside light observing signal is input.

8. An endoscope apparatus according to claim 2 wherein said light amount increasing means has a plurality of optical members inserted in said light path of the illuminating light leading to said rotary filter means for detouring said light path from said rotary filter means.

9. An endoscope apparatus according to claim 2 wherein said light amount increasing means further comprises a lamp illuminated when said body outside light observing signal is input.

10. An endoscope apparatus according to claim 9 wherein said lamp is arranged in said light path.

11. An endoscope apparatus according to claim 1 wherein said illuminating light feeding means comprises a light source lamp for generating said illuminating light and a lamp controlling means for feeding electric power to said light source lamp.

12. An endoscope apparatus according to claim 11 wherein said light amount increasing means comprises an iris means for adjusting the illuminating light output from said illuminating light feeding means.

13. An endoscope apparatus according to claim 2 or 3 wherein said lamp controlling means increases the light amount output from said light source lamp when said body outside light observing is input.

14. An endoscope apparatus according to claim 1 wherein said light amount increasing means comprises and operating means which starts counting said preset time when said body outside light observing signal is input and increases the light amount of said illuminating light for said preset time.

15. An endoscope apparatus comprising:
an endoscope including an insertable part to be inserted into a body cavity, said insertable part having a tip part provided with an observing window for observing an object to be imaged and an illuminating window for emitting an illuminating light to illuminate said object;
imaging means in said endoscope for viewing said illuminated object; and
a light source apparatus including an illuminating light feeding means for generating an illuminating light to be fed to said endoscope for illuminating said object in said body cavity, and a light amount increasing means for increasing the light amount of the illuminating light generated by said illuminating light feeding means; and
a body outside light observing signal generating means for generating said body outside light observing signal;
wherein said light amount increasing means increases the light amount for a preset time when said body outside light observing signal is input for confirming from outside the body a position within the body of said endoscope tip part;
said light amount being increased to a level such that the light can be viewed through the body from outside the body to confirm said tip position, and said preset time being set such that the increased light amount is discontinued before body tissue is burned by heat from said light source.

16. An endoscope apparatus according to claim 15 wherein said illuminating light feeding means comprises a light source lamp for generating said illuminating light, a lamp controlling means for feeding electric power to said light source lamp and a rotary filter means inserted in a light path of the illuminating light output from said light source lamp for separating said illuminating light into color lights for color-photographing.

17. An endoscope apparatus according to claim 16 wherein said light amount increasing means comprises a filter moving means for retreating said rotary filter means from the light path and an iris means for adjusting the illuminating light out output from said illuminating light feeding means.

18. An endoscope apparatus according to claim 17 wherein said light amount increasing means further comprises a turret means comprising at least a filter for reducing the light amount of the illuminating light generated by said illuminating light feeding means and an infrared ray cutting filter for removing an infrared ray component of said illuminating light.

19. An endoscope apparatus according to claim 16 wherein said rotary filter means has red, green and blue color separating filters for separating the illuminating light into color lights for color-photographing.

20. An endoscope apparatus according to claim 16 wherein said rotary filter means has red and blue color separating filters for separating the illuminating light into color lights for color-photographing and a filter for transmitting a white color light.

21. An endoscope apparatus according to claim 20 wherein said illuminating light feeding means further has a controlling circuit for position said filter transmitting the white color light in the light path when said body outside light observing signal is input.

22. An endoscope apparatus according to claim 16 wherein said light amount increasing means has a plurality of optical members inserted into said light path of the illuminating light leading to said rotary filter means when said body outside light observing signal is input for detouring said light path from said filter means.

23. An endoscope apparatus according to claim 16 wherein said light amount increasing means further comprises a lamp illuminated when said body outside light observing signal is input.

24. An endoscope apparatus according to claim 23 wherein said lamp is arranged in said light path.

25. An endoscope apparatus according to claim 15 wherein said illuminating light feeding means comprises a light source lamp for generating said illuminating light and a lamp controlling means for feeding electric power to said light source lamp.

26. An endoscope apparatus according to claim 25 wherein said light amount increasing means comprises an iris means for adjusting the illuminating light output from said illuminating light feeding means.

27. An endoscope apparatus according to claim 16 or 25 wherein said lamp controlling means increases the light amount output by said light source lamp when said body outside light observing signal is input.

28. An endoscope apparatus according to claim 15 wherein said signal processing means comprises a driving circuit for driving said imaging means, a processing circuit for processing an electric signal of said-imaging means to produce a standard video signal and an operating means for placing said driving circuit and signal processing circuit in a device shutter mode when said body outside light observing signal is input.

29. An endoscope apparatus according to claim 15 wherein said endoscope has a curving mechanism for curving said insertable part.

30. An endoscope apparatus according to claim 29 wherein said endoscope has a sensor for detecting the operation of said curving mechanism.

31. An endoscope apparatus according to claim 30 wherein said light amount increasing means continues to increase the light amount for an additional time period of the preset time when operation of said curving mechanism is detected by said sensor.

32. An endoscope apparatus according to claim 15 wherein said imaging means is a solid state imaging device provided within said insertable part for converting to an electric signal an object image taken through said observing window.

33. An endoscope apparatus according to claim 15 wherein said imaging means is a television camera removably fitted to said endoscope.

34. An endoscope apparatus according to claim 33 wherein said endoscope has within the insertable part an optical image transmitting means for optically transmitting an object image taken through said observing window.

* * * * *